(12) United States Patent
Biswas et al.

(10) Patent No.: US 10,702,591 B2
(45) Date of Patent: *Jul. 7, 2020

(54) THERAPEUTIC CANCER VACCINE TARGETED TO HAAH (ASPARTYL-[ASPARAGINYL]-BETA-HYDROXYLASE

(71) Applicant: Panacea Pharmaceuticals, Inc., Gaithersburg, MD (US)

(72) Inventors: Biswajit Biswas, Germantown, MD (US); Carl R. Merril, Bethesda, MD (US); Hossein Ghanbari, Gaithersburg, MD (US)

(73) Assignee: Panacea Pharmaceuticals, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/666,947

(22) Filed: Aug. 2, 2017

(65) Prior Publication Data

US 2018/0092969 A1   Apr. 5, 2018

Related U.S. Application Data

(63) Continuation of application No. 14/073,210, filed on Nov. 6, 2013, now Pat. No. 9,744,223, which is a (Continued)

(51) Int. Cl.
*A61K 39/00* (2006.01)
*C07K 14/47* (2006.01)
*C12N 9/02* (2006.01)

(52) U.S. Cl.
CPC ...... *A61K 39/0011* (2013.01); *C07K 14/4748* (2013.01); *C12N 9/0071* (2013.01); *A61K 2039/5256* (2013.01); *A61K 2039/53* (2013.01); *A61K 2039/6075* (2013.01); *C07K 2319/735* (2013.01); *C12N 2795/10342* (2013.01); *C12N 2795/10343* (2013.01); *C12Y 114/11016* (2013.01)

(58) Field of Classification Search
None
See application file for complete search history.

(56) References Cited

U.S. PATENT DOCUMENTS 7,745,391 B2  6/2010 Mintz et al.
9,744,223 B2 * 8/2017 Biswas ............ A61K 39/0011
(Continued)

FOREIGN PATENT DOCUMENTS

WO   WO-2007/076101 A2   7/2007

OTHER PUBLICATIONS

Biswas, B. et al., "Dendritic Cell-Based Cancer Therapeutic Vaccine Targeting HAAH Using Nano-Particles to Overcome Tolerance and Avoid Auto-Immune Response," J. Immunother., (2010), vol. 33, No. 8, pp. 874-875.

(Continued)

*Primary Examiner* — Michelle S Horning
(74) *Attorney, Agent, or Firm* — Cooley LLP; Ivor Elrifi

(57) ABSTRACT

The present invention encompasses a cancer vaccine therapy targeting Aspartyl-[Asparaginyl]-,8-hydroxylase (HAAH). The present invention contemplate bacteriophage expressing HAAH peptide fragments and methods for using said bacteriophage in methods of treating cancer.

6 Claims, 21 Drawing Sheets

Specification includes a Sequence Listing.

In vitro expression of antigen prior to inoculation in animals

Designing lambda system to display antigenic proteins as a C terminus fusion product of gpD

Related U.S. Application Data continuation-in-part of application No. 13/836,487, filed on Mar. 15, 2013, now abandoned.

(56) References Cited

U.S. PATENT DOCUMENTS

| | | | |
|---|---|---|---|
| 2002/0110559 | A1 | 8/2002 | Wands et al. |
| 2005/0123545 | A1 | 6/2005 | Wands et al. |
| 2005/0226892 | A1 | 10/2005 | Rao |
| 2007/0207167 | A1* | 9/2007 | Merril .................... A61K 39/12 424/199.1 |
| 2008/0305119 | A1 | 12/2008 | Dewhurst et al. |
| 2010/0172832 | A1 | 7/2010 | Wands et al. |
| 2014/0271689 | A1 | 9/2014 | Biswas et al. |
| 2014/0271691 | A1 | 9/2014 | Biswas et al. |
| 2014/0356930 | A1 | 12/2014 | Ghanbari |
| 2017/0072034 | A1 | 3/2017 | Biswas et al. |
| 2018/0036424 | A1* | 2/2018 | Ghanbari ........... A61K 47/6811 |

OTHER PUBLICATIONS

Buus, et al., "High-resolution Mapping of Linear Antibody Epitopes Using Ultrahigh-density Peptide Microarrays," Molecular & Cellular Proteomics 11.12, pp. 1790-1800.

Dinchuk, Je et al., Aspartyl β-Hydroxlase (Asph) and an Evolutionarily Conserved isoform of Asph Missing the Catalytic Domain Share Exon with Junctin. The Journal of Biological Chemistry, Aug. 23, 2000, vol. 275, pp. 39543-39554.

GenBank; ACD93450.1 Aspartate beta-hydroxylase isoform f (*Homo sapiens*). (Jun. 10, 2008) downloaded from the internet http://www.ncbi.nlm.nih.gov/protein/189409315?report=genbank&log$=protalign&blast_rank=1&RID=4UTUDPRZ01R, 1 page.

Ghaemi et al. "Recombinant λ-phage nanobioparticles for tumor therapy in mice models," Genetic Vaccines and Therapy, 2010, 8, 1-7.

Ghanbari, H. and Lebowitz, M., "In vivo efficacy of PAN-622: An all human sequence monoclonal antibody targeted at HAAH," Cancer Res., (2008), vol. 68, No. 9, Suppl., Abstract 3979.

Gupta et al., "High-density Functional Display of Proteins on Bacteriophage Lambda," J. Mol. Biol. (2003) 334, 241-254.

Hoess, "Bacteriophage Lambda as a Vehicle for Peptide and Protein Display," Current Pharmaceutical Biotechnology, 2002, 3, 23-28.

International Search Report and Written Opinion dated Aug. 22, 2014, for PCT/US2014/030551, 7 pages.

Korioth et al., "Cloning and characterization of the human gene encoding aspartyl β-hydroxylase," Gene, 1994, 150:395-399.

Lavaissiere et al., "Overexpression of Human Aspartyl(Asparaginyl) β-Hydroxylase in Hepatocellular Carcinoma and Cholangiocarcinoma," J. Clinical Investigation, 1996, 98:1313-1323.

Mikawa et al., "Surface Display of Proteins on Bacteriophage Heads," J. Mol. Biol. (1996) 262, 21-30.

Noda et al., "Immunization with Aspartate-β-Hydroxylase-Loaded Dendritic Cells Produces Antitumor Effects in a Rat Model of Intrahepatic Cholangiocarcinoma," Hepatology, (2012), vol. 55, No. 1, pp. 86-97.

Stolz et al., "Bacteriophage lambda surface display of a bacterial biotin acceptor domain reveals the minimal peptide size required for biotinylation," FEBS Letters, 1998, 440:213-217.

Tomimaru et al., "Aspartate-β-hydroxylase induces epitope-specific T cell responses in hepatocellular carcinoma," Vaccine 33 (2015), pp. 1256-1266.

Yang et al., "Novel Fold and Capsid-Binding Properties of the λ-phage Display Platform Protein gpD," Nature Structural Biology, Mar. 2000 vol. 7 pp. 230-237.

Yeung, Y. A. et al., Isolation and characterization of human antibodies targeting human aspartyl (asparaginyl) β-hydroxylase, Human Antibodies, (2007), vol. 16, pp. 163-176.

Bahadir, A.O. et al., "Phage Displayed HBV Core Antigen with Immunogenic Activity," Appl. Biochem Biotechnol., (2011), vol. 165, pp. 1437-1447.

Bazan et al., "Phage display—A powerful technique for immunotherapy," Human Vaccines & Immunotherapeutics 8:12, 1817-1827; Dec. 2012.

Final Program for 25th Annual Scientific Meeting, International Society for Biological Therapy of Cancer (iSBTc), (2010), Page Front, 1, 3, 6, 59, [retrieved on Nov. 21, 2019], Retrieved from the Internet, Society for Immunotherapy of Cancer Web site, URL, https://sitc.sitcancer.org/meetings/am10.

Mattiacio, J. et al., "Dense display of HIV-1 envelope spikes on the lambda phage scaffold does not result in the generation of improved antibody responses to HIV-1 Env," Vaccine, (2011), vol. 29, No. 14, pp. 2637-2647.

Piersanti, S. et al., "Mammalian cell transduction and internalization properties of phages displaying the full-length adenoviral penton base or its central domain," J. Mol. Med., (2004), vol. 82, pp. 467-476.

Ren, S. et al., "Inhbition of tumor angiogenesis in lung cancer by T4 phage surface displaying mVEGFR2 vaccine," Vaccine, (2011), vol. 29, pp. 5802-5811.

Xiao-Hui, L. et al., "Antitumor Effect of Recombinant T7 Phage Vaccine Expressing Xenogenic Vascular Endothelial Growth Factor on Lewis Lung Cancer in Mice," Chinese Journal of Cancer, 2006, 25 (10), 1221-1226 (with English language abstract).

Biswas, B. et al., "Dendritic Cell-Based Cancer Therapeutic Vaccine Targeting HAAH Using Nano-Particles to Overcome Tolerance and Avoid Auto-Immune Response," International Society for Biological Therapy of Cancer, Oct. 2-4, 2010, 13 pages.

* cited by examiner

In vitro expression of antigen prior to inoculation in animals

Designing lambda system to display antigenic proteins as a C terminus fusion product of gpD

```
                                                                              *************
HAAH_Human    MAQRKNAKSSG-NSSSSGSGSGS------------TSAGSSSPGARRETKHGGHKNGRKGGLSGTSFFTWFMVIALLGVWTSVA    71
AAH_Rat       ----------------------------------------------------------------MVIALLGVWTSVA           13
AAH_mouse     MAPRKNAKGGGGNSSSSGSGSGSGSGSPSTGSSGSSSSPGARREAKHGGHKNGRRGGISGGSFFTWFMVIALLGVWTSVA          80
AAH_Chicken   MASRKGSKGTG-------------------GAPGPGSKRESKHGGNRNGKKEGLSGSSFFTWFMVIALLGVWTSVA              57
                                                             ▼ 1 start

****:********,.          ***:**********:*********** .*  . .*.  *  :  **
HAAH_Human    VVWFDLVDYEEVLG------------KLGIYDADGDGDFDVDDAKVLLGLKERSTSEPAVPPEE--AEPHTEPEEQVP          135
AAH_Rat       VVWFDLVDYEEVLG------------KLGIYDADGDGDFDVDDAKVLLGLKERSTSERTFPPEE--AETQAELEEQAP           77
AAH_mouse     VVWFDLVDYEEVLG------------KLGIYDADGDGDFDVDDAKVLLGLKERSPSERTFPPEEEAETHAELEEQAP          145
AAH_Chicken   VVWFDLVDYEEVLAKAKDFRYNLSEVLQGKLGIYDADGDGDFDVEDAKVLLGLKERSVPEQPASPVS---EETIQPAEQSF       135

:: :*::  *  :*:**.:*:: :*::         *  :..:*   * ::      * : :*        . : *.  ..
HAAH_Human    VEAEPQNIEDEAKEQIQSLLHEMVHAEHVEGEDLQQEDGPTGEP-QQEDDEFLMATDVDDRFHTLEPEVSHEETEHSYHV       214
AAH_Rat       EGASAQNVEDEVKEQIQSLLQESVHTDHD------LEADGPAGEP-QSEVEDFLTATDSDDRFEALEPGTVHEDTEDSYHV      151
AAH_mouse     EGADIQNVEDEVKEQIQSLLQESVHTDHD------LEADGLAGEP-QPEVEDFLTVTDSDDRFEDLEPGTVHEEIEDTYHV      219
AAH_Chicken   TKSEHKNVDVELEEEIQPVLHDALHSQPD------ADFVADDPGATEPETYEVPGDSELTLEDAVEHYTEPEYEKETET       208

::*,. ::  ::.*  .  ..          : *   ::    **,. .*   ::            . .: :
HAAH_Human    EETVSQDCNQDMEEMMSEQENPDSSEPVVEDERLHHDTDDVTYQVYEEQA-VYEPLENEGIEITEVTAPPEDNPVEDSQV       293
AAH_Rat       EETASQNHPNDAEEVMSEQES-------------SEEVRHEDYDEP---VYEPSENERIEIS-----------DNAIDDSNI     206
AAH_mouse     EDTASQNHPNDMEEMTNEQEN-------------SEEVRHQDYDEP---VYEPSEHEGVAIS-----------DNTIDDSSI     274
AAH_Chicken   QDTAVEDLPEEVHEATEPVRD-----------------ETVEDLEMEKKLPVVESKHTEEDNVAT---------GPEESEVPV    265
                                                         ▼ 1 end                ▼ 2 start
              *:.    :  :   :..                 *******************************:**:***: *:  **.:**:
HAAH_Human    IVEEVSIFPVEEQQEVPPETNRKTDDPEQKAKVKKKKKPKLLNKFDKTIKAELDAAEKLRKRGKIEEAVNAFKELVRKYPQ       373
AAH_Rat       ISEEINVASVEEQQDTPP-----------------VKKKKPKLLNKFDKTIKAELDAAEKLRKRGKIEEAVSAFEELVRRYPQ    272
AAH_mouse     ISEEINVASVEEQQDTPP-----------------VKKKKPKLLNKFDKTIKAELDAAEKLRKRGKIEEAVNAFEELVRKYPQ    340
AAH_Chicken   QTEDYSNDNLVGKCETETEQDK------------MEKVKKKKKPKLLNKFDKTIKAELDAAEKLRKRGKVEEALRAFEALVNQYPE   339

**********,.****** ****:*: **:**:*,.**:.*:**:********,.::.*****:.****;*:******.*
HAAH_Human    SPRARYGKAQCEDDLAEKRRSNEVLRGAIETYQEVASLPDVPADLLKLSLKRRSDRQQFLGHMRGSLLTLQRLVQLFPND       453
AAH_Rat       SPRARYGKAQCEDDLAEKQRSNEVLRRAIETYQEAASLPDAPTDLVKLSLKRRSERQQFLGHMRGSLLTLQRLVQLFPSD       352
AAH_mouse     SPRARYGKAQCEDDLAEKQRSNEVLRRAIETYQEAADLPDAPTDLVKLSLKRRSERQQFLGHMRGSLLTLQRLVQLFPSD       420
AAH_Chicken   SPRARYGKAQSEDDLAEKMRSNEMLQKAINTYDEVVSLPNVPSDLIKLSLKREADRQQFLGRMRGSLITLQKLVHLFPSD       419
```

FIG. 2

↓ 2 end

```
              *:************:***..**:******  ::*:*************:*:*:********:******************
HAAH_Human    TSLKNDLGVGYLLIGDNDNAKKVYEEVLSVTPNDGFAXVHYGFILKAQNKIAESIPYLKEGIESGDPGTDDGRFYFHLGD    533
AAH_Rat       TTLKNDLGVGYLLMGDNDSAKKVYEEVLNVTPNDGFAXVHYGFILKAQNRIAESIPYLKEGIESGDPGTDDGRFYFHLGD    432
AAH_mouse     TTLKNDLGVGYLLLGDNDSAKKVYEEVLNVTPNDGFAXVHYGFILKAQNKISESIPYLKEGIESGDPGTDDGRFYFHLGD    500
AAH_Chicken   TSFKNDLGVGYLLIGDNSNAKQVYEEVLRMAPDDGFAXVHYGFILKAENKIAESIPYLKEGLESGDPGTDDGRFYFHLGD    499
```
↓ 3 start

```
              *:**:*:**********::************ **:******    .:*****:******:******** ****::.***
HAAH_Human    AMQRVGNKEAYKWYELGHKRGHFASVWQRSLINVNGLKAQPCG--PKETGYTQLVKSLERNWKLIRDEGLAVMDKAKGLFL    612
AAH_Rat       AMQRVGNKEAYKWYELGHKRGHFASVWQRSLYNVNGLKAQPWWTPRETGYTELVKSLERNWKLIRDEGLMVMDKAKGLFL    592
AAH_mouse     AMQRVGNKEAYKWYELGHKRGHFASVWQRSLYNVNGLKAQPWWTPRETGYTELVKSLERNWKLIRDEGLMVMDKAKGLFL    580
AAH_Chicken   ALQRIGDKEAYKWYELGYQRGHFASVWQRSLYNVKGLKAQPWWTAKETGYTELVKSLEKNWKLIRDEGLDVMDKKRSLFL    579

**********************:*******.****:***:*.*:**********:* ***********************
HAAH_Human    PEDENLREKGDWSQFTLWQQGRRNENACKGAPKTCTLLEKFPETTGCRRGQIKYSIMHPGTHVWPHTGPTNCRLRMHLGL    692
AAH_Rat       PEDENLREKGDWSQFTLWQQGRKNENACKGAPKTCTLLEKFSETTGCRRGQIKYSIMHPGTHVWPHTGPTNCRLRMHLGL    592
AAH_mouse     PEDENLREKGDWSQFTLWQQGRKNENACKGAPKTCALLEKFSETTGCRRGQIKYSIMHPGTHVWPHTGPTNCRLRMHLGL    660
AAH_Chicken   PEDENLREKGDWSQFTLWQQGRKNENACKGVPKTCALLERFPEATGCRRGQIKYSVMLPGTHVWPHTGPTNCRLRMHLGL    659
```
↓ 3 end

```
              *******:****:*.::******.***********.*:*************.****:****
HAAH_Human    VIPKEGCKIRCANETKTWEEGKVLIFDDSFEHEVWQDASSFRLIFIVDVWHPELTPQQRRSLPAI    757
AAH_Rat       VIPKEGCKIRCANETRSWEEGKVLIFDDSFEHEVWQDASSFRLIFIVDVWHPELTPQQRRSLPAI    657
AAH_mouse     VIPKEGCKIRCANETRTWEEGKVLIFDDSFEHEVWQDASSFRLIFIVDVWHPELTPQQRRSLPAI    725
AAH_Chicken   VIPKEGCRIRCAQENRTWEEGKVLIFDDSFEHEVWQDAESYRLIFIVDVWHPELTAQQRRSLPAI    724
```

FIG. 2 (Continued)

- Tumors established Day-3 with 10⁷ FOCUS cells (hepatic cancer cell line)
- Antibody injected IV 3X/wk, Days 0-25 (last injection marked with arrow)
- 5 of 12 PAN-622 treated animals reached undetectable tumor volume, a direct evidence of cytotoxic effect Map HAAH–Construct I

```
DRAMAQRKNAKSSGNSSSSGSGSGSTSAGSSSPGARRETKHGGHKNGRKG 50
GLSGTSFFTWFMVIALLGVWTSVAVVWFDLVDYEEVLGKLGIYDADGDGD 100
FDVDDAKVLLGLKERSTSEPAVPPEEAEPHTEPEEQVPVEAEPQNIEDEA 150
KEQIQSLLHEMVHAEHVEGEDLQQEDGPTGEPQQEDDEFLMATDVDDRFE 200
TLEPEVSHEETEHSYHVEETVSQDCNQDMEEMMSEQENPDSSEPVVEDER 250
LHHDTDDVTYQVYEEQAVYEPLENEGIEITEVTAPPEDNPVEDSQVIVEE 300
VSIFPVEEQQEVPP
```

Map HAAH–Construct II

```
                                              LDA 350
AEKLRKRGKIEEAVNAFKELVRKYPQSPRARYGKAQCEDDLAEKRRSNEV 400
LRGAIETYQEVASLPDVPADLLKLSLKRRSDRQQFLGHMRGSLLTLQRLV 450
QLFPNDTSLKNDLGVCYLLIGDNDNAKKVYEEVLSVTPNDGFAKVHYGFI 500
LKAQNKIAESIPYLKEGIESGDP
```

Map HAAH–Construct III

```
                   GTDDGRFYFHLGDAMQRVGNKEAYKWY 550
ELGHKRGHFASVWQRSLYNVNGLKAQPWWTPKETGYTELVKSLERNWKLI 600
RDEGLAVMDKAKGLFLPEDENLREKGDWSQFTLWQQGRRNENACKGAPKT 650
CTLLEKFPETTGCRRGQIKYSIMHPGTHVWPHTGPTNCRLRMHLGLVIPK 700
EGCKIRCANETRTWEEGKVLIFDDSFEHEVWQDASSFRLIFIVDVWHPEL 750
TPQQRRSLPAI*HEFMQAWET
```

THERAPEUTIC CANCER VACCINE TARGETED TO HAAH (ASPARTYL-[ASPARAGINYL]-BETA-HYDROXYLASE

RELATED APPLICATIONS

This application is a continuation of U.S. patent application Ser. No. 14/073,210 filed Nov. 6, 2013 (granted as U.S. Pat. No. 9,744,223) which is a continuation-in-part of U.S. patent application Ser. No. 13/836,487, filed Mar. 15, 2013, the disclosure of each of which is hereby incorporated in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 091150.00019CIP_SL.txt, date recorded: Nov. 21, 2017, file size 32,299 bytes).

BACKGROUND OF THE INVENTION

Cancer is one of the most devastating diseases both in terms of human life opportunity loss and health care cost. It also presents unmet clinical needs. Currently available chemotherapies have limited efficacy and limited target patient population. Even the successful immunotherapies have shortcomings similar to chemotherapies. Moreover, essentially all cancer therapeutics have significant adverse side effects.

Aspartyl-(Asparaginyl)-β-hydroxylase (HAAH) is over expressed in various malignant neoplasms, including hepatocellular and lung carcinomas. HAAH is a tumor specific antigen, which is specifically expressed on the surface of certain malignant cells. HAAH is a hydroxylation enzyme that modifies factors such as Notch that contribute to cancer etiology by causing cell proliferation, motility, and invasiveness. Neutralizing the enzyme or reducing its expression leads to normal phenotype(s) in cancer cells. Anti-HAAH antibodies (as well as siRNA) have been shown to be cytostatic. An all-human sequence anti-HAAH (PAN-622) has shown to inhibit tumor growth by more than 90% in animal studies by passive immunotherapy. However, HAAH is well conserved and is also over expressed in placenta hence it is not sufficiently immunogenic in animals and it is certainly a self antigen in humans.

A vaccine therapy targeted to a pan-cancer-specific antigen such as HAAH that has proven relevance to cancer etiology is very desirable. Its economic impact will be enormous both in terms of job creation and increased productivity as well as in savings in health care and extending productive lives. The vaccine therapy of the present invention is novel both in terms of its target and the vaccine entity.

SUMMARY OF THE INVENTION

The present invention encompasses a cancer vaccine therapy targeting human Aspartyl-[Asparaginyl]-β-hydroxylase (HAAH).

Certain embodiments of the present invention contemplate bacteriophage expressing HAAH peptide fragments, wherein the bacteriophage may be any one of Lambda, T4, T7, or M13/fl.

The present invention further contemplates methods of treating cancer comprising stimulating the immune system of a patient with bacteriophage expressing HAAH fragments.

The present invention also contemplates nano-particles comprising at least one amino acid sequence native to HAAH.

The present invention also encompasses methods for treating cancer comprising the step of providing an immune system stimulating amount of a Lambda phage to a patient, wherein the Lambda phage comprises amino acid sequences native to HAAH expressed on its surface.

The present invention also encompasses methods for treating cancer comprising the step of providing an immune system-stimulating amount of a nano-particle to a patient, wherein the nano-particle comprises amino acid sequences native to HAAH.

One embodiment of the present invention contemplates bacteriophage comprising at least one amino acid sequence native to HAAH, wherein the at least one amino acid sequence native to HAAH is selected from the group consisting of the amino acid sequence of Construct I, the amino acid sequence of Construct II and the amino acid sequence of Construct III.

The present invention also contemplates a Lambda phage expressing the amino acid sequence of Construct I, the amino acid sequence of Construct II or the amino acid sequence of Construct III on its surface.

Embodiments of the present invention also contemplate nucleic acid construct comprising at least one nucleotide sequence encoding an amino acid sequence native to HAAH and a nucleic acid sequence encoding bacteriophage lambda head decoration protein D (hereinafter "gpD").

Another embodiment of the present invention includes nucleic acid constructs comprising nucleotide sequences encoding the amino acid sequence of Construct I, the amino acid sequence of Construct II or the amino acid sequence of Construct III.

BRIEF DESCRIPTION OF THE FIGURES

FIG. 2 provides a comparison of AAH amino acid sequences (SEQ ID NOS:3-6, respectively, in order of appearance).

FIG. 19 shows amino acid sequences in accordance with an embodiment of the present invention. Construct I: SEQ ID NO:7. Construct II: SEQ ID NO:8. Construct III: SEQ ID NO:9. HEFMQAWET: SEQ ID NO:10.

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implemented in other systems, and that any such variation would be within such modifications that do not part from the scope of the present invention. Before explaining the disclosed embodiments of the present invention in detail, it is to be understood that the invention is not limited in its application to the details of any particular arrangement shown, since the invention is capable of other embodiments. The terminology used herein is for the purpose of description and not of limitation. Further, although certain methods are described with reference to certain steps that are presented herein in certain order, in many instances, these steps may be performed in any order as would be appreciated by one skilled in the art, and the methods are not limited to the particular arrangement of steps disclosed herein.

The present invention is based on the discovery that bacteriophage surface-expressed HAAH is highly immunogenic and could overcome tolerance of self antigen because of altered presentation and the adjuvant function of bacteriophage itself. The present invention provides a cancer vaccine therapy targeting HAAH using bacteriophage-expressed HAAH fragments.

Figure 1:
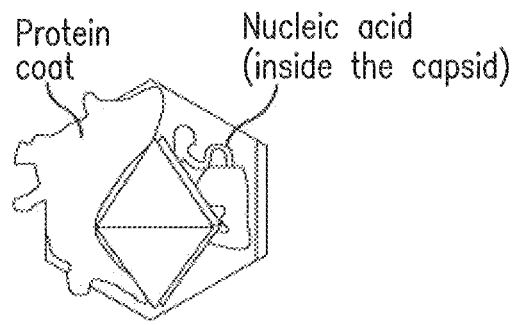
FIG. 1 is a representation of the in vitro expression of an antigen.
Figure 3:
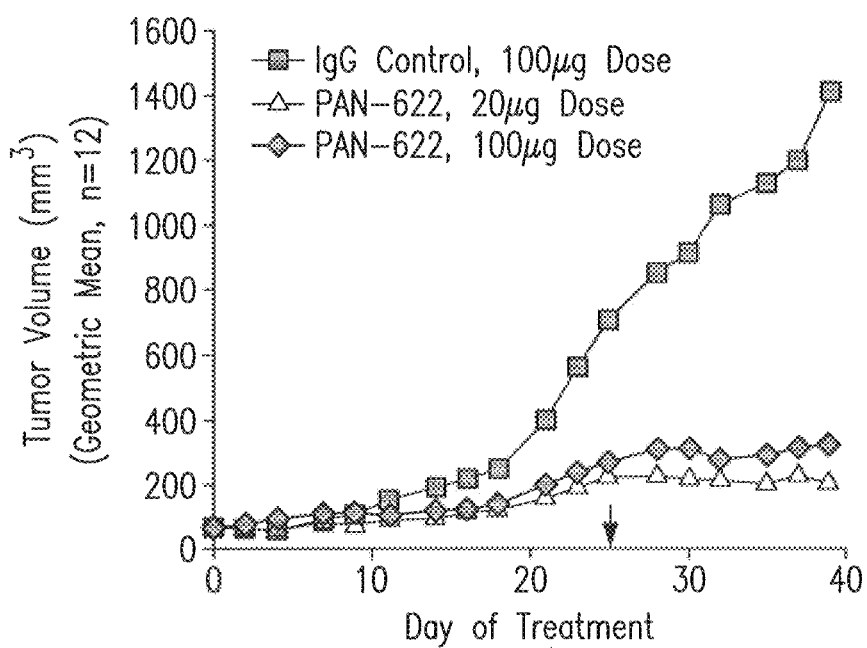
FIG. 3 is a graph that demonstrates the efficacy of an antibody against HAAH in liver cancer cells.
Figure 4:
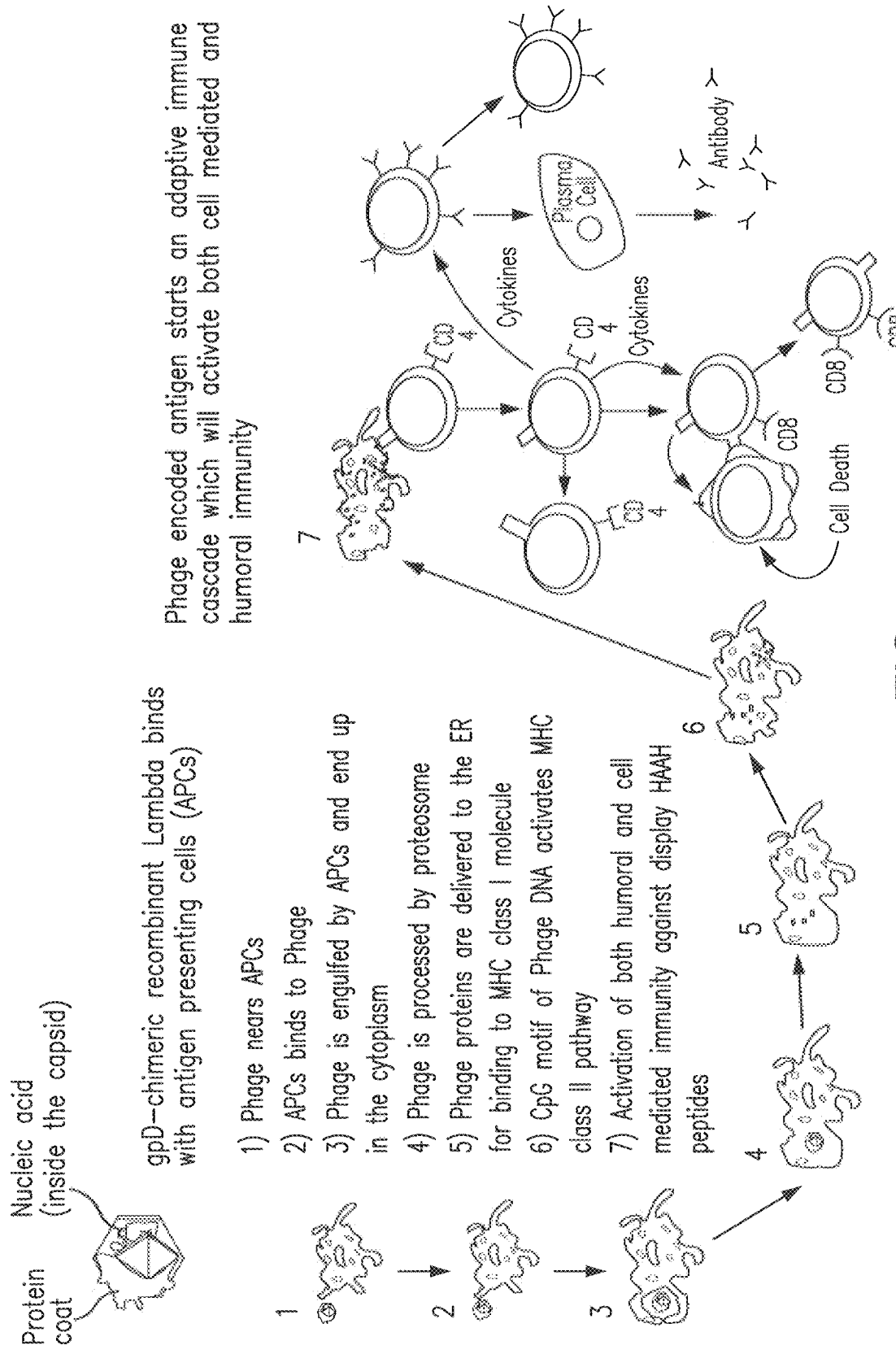
FIG. 4 shows the mechanism of immunization in accordance with the present invention.
Figure 5:
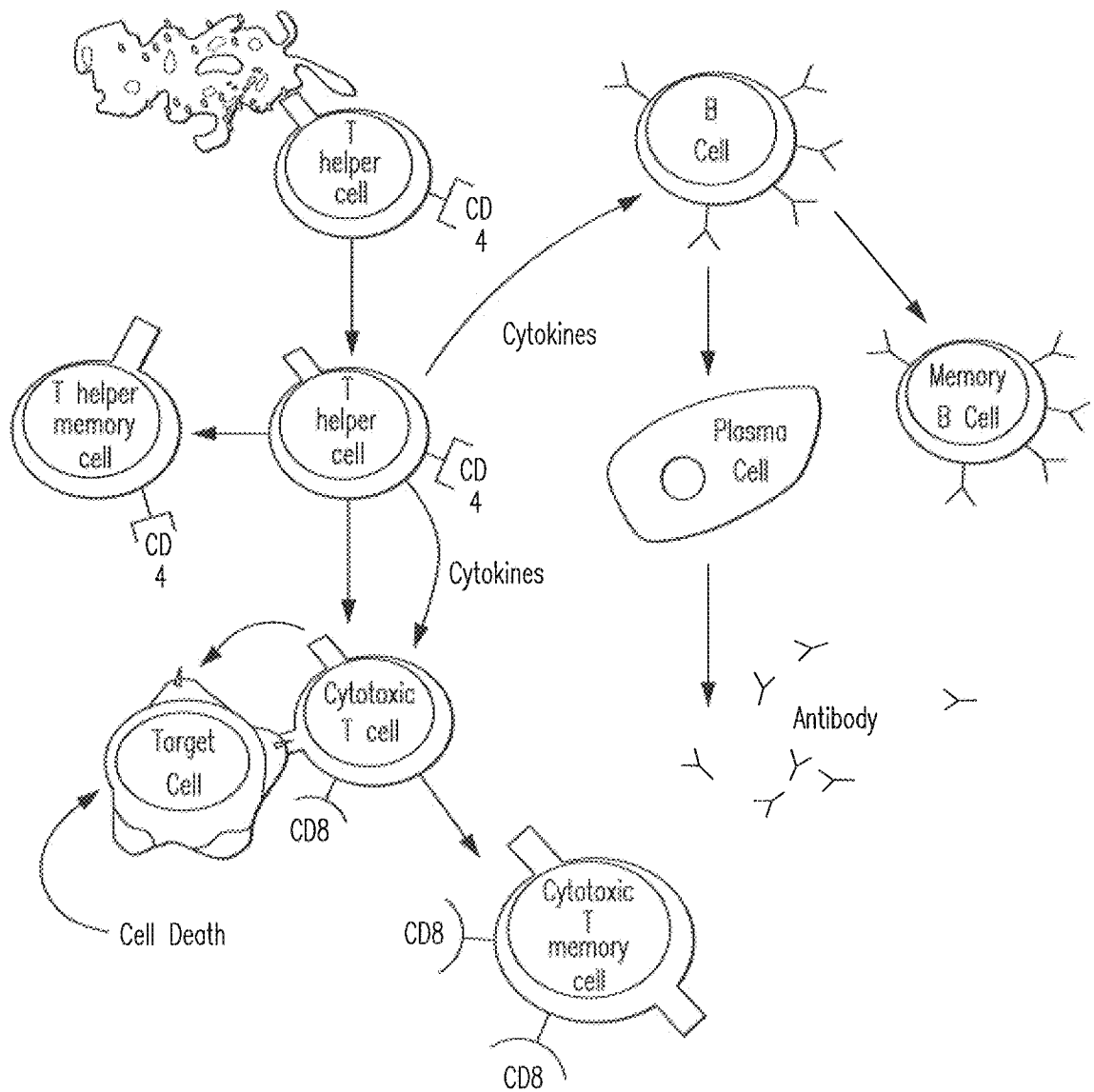
FIG. 5 shows the immune response.
Figure 6A:
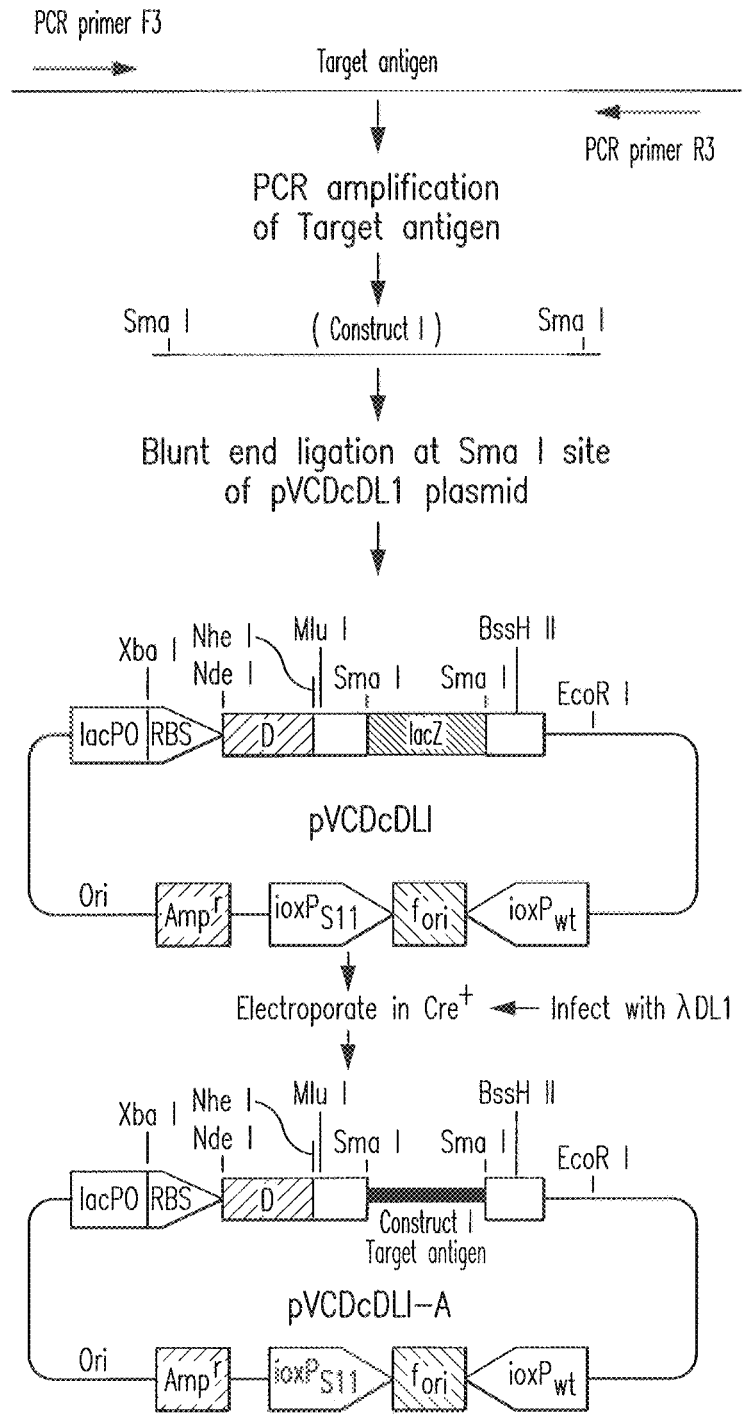
FIG. 6 A-B Homologous recombination of donor plasmid pAN-A- with recipient phage vector. Only some of the lambda genes are shown. The unique Nhe I and Bssh II site in the lambda genome used for cloning is shown as is lacZa, a DNA cassette comprised of lacPO, RBS and the first 58 codons of lacZ. Generated recombinant phages are designated as HAAH construct I, II and III which contains an insert of HAAH fragment. Only diagram of construct I is shown here. The insert is fused with gpD head protein gene of lambda to produce gpD-HAAH construct I fusion on lambda capsid. The maps are not to scale.
Figure 6B:
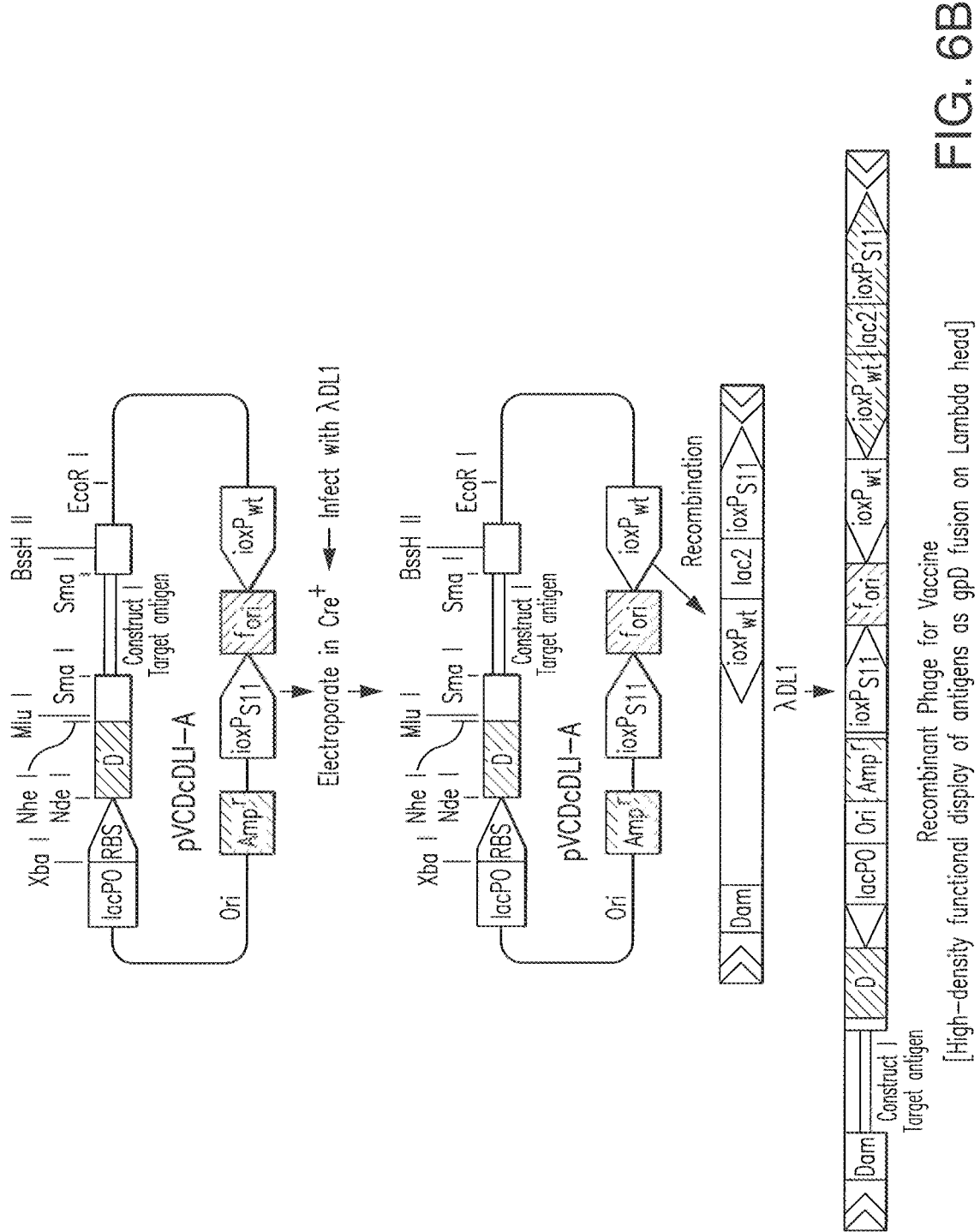

It has been shown that passive immunotherapy using an all-human anti-HAAH is effective in cellular and animals models of cancer (in nude mice model, FIG. 1). The present invention demonstrates that bacteriophage delivery of HAAH fragments as vaccine can overcome the problem of self antigen tolerance by providing novel antigen presentation and inherent phage adjuvant properties.

In vitro activation of dendritic cells by tumor antigens, prior to administration to patient body shows promising results for cancer therapy. Unfortunately the process is cumbersome, expensive and time consuming for mass scale immune therapy against various cancers. Bacteriophage display is a simple way of achieving favorable presentation of peptides to the immune system. Previous findings revealed that recombinant bacteriophage can prime strong CDS+ T lymphocytes (CTLs) responses both in vitro and in vivo against epitopes displayed in multiple copies on their surface, activate T-helper cells and elicit the production of specific antibodies all normally without adjuvant.

As proposed herein, vaccination with lambda phage-displaying cancer specific antigen such as HAAH has a number of potential advantages. One of the advantages is display of multiple copies of peptides on the same lambda phage, and once the initial phage display has been made, subsequent production should be far easier and cheaper than the ongoing process of coupling peptides to carriers. There is also good evidence that due to particulate nature, phage-displayed peptides can access both the major histocompatibility complex (MHC) I and MHC II pathway, suggesting lambda phage display vaccines can stimulate both cellular and humoral arms of the immune system, although as extra cellular antigens, it is to be expected that the majority of the responses will be antibody (MHC class II) biased. It has been shown that particulate antigens, and phage in particular, can access the MHC I pathway through cross priming, and it is likely that it is this process which is responsible for stimulating a cellular response. This added cellular response mediated by CDS+ T cells helps to eliminate the cancer cells. Also, the role of Innate immunity in cancer is well established fact. Lambda phage can also act as nonspecific immune stimulators. It is likely that a combination of the foreign DNA (possibly due to the presence of CpG motifs) and the repeating peptide motif of the phage coat are responsible for the nonspecific immune stimulation. As a summary: whole lambda phage particles possess numerous intrinsic characteristics which make them ideal as vaccine delivery vehicles. For use as phage display vaccines, the particulate nature of phage means they should be far easier and cheaper to purify than soluble recombinant proteins since a simple centrifugation/ultra-filtration and column chromatography step should be sufficient to remove the majority of soluble contaminants. Additionally, the peptide antigen comes already covalently conjugated to an insoluble immunogenic carrier with natural adjuvant properties, without the need for complex chemical conjugation and downstream purification processes which must be repeated with each vaccine batch.

The present invention provides a prophylactic and therapeutic "phage vaccine" for both cancer prevention and treatment. In the present invention, fragmented HAAH peptides are successfully displayed on the surface of lambda head and large scale production and purification is carried out to perform animal experiments. The detail of these procedures is depicted below.

Figure 7:
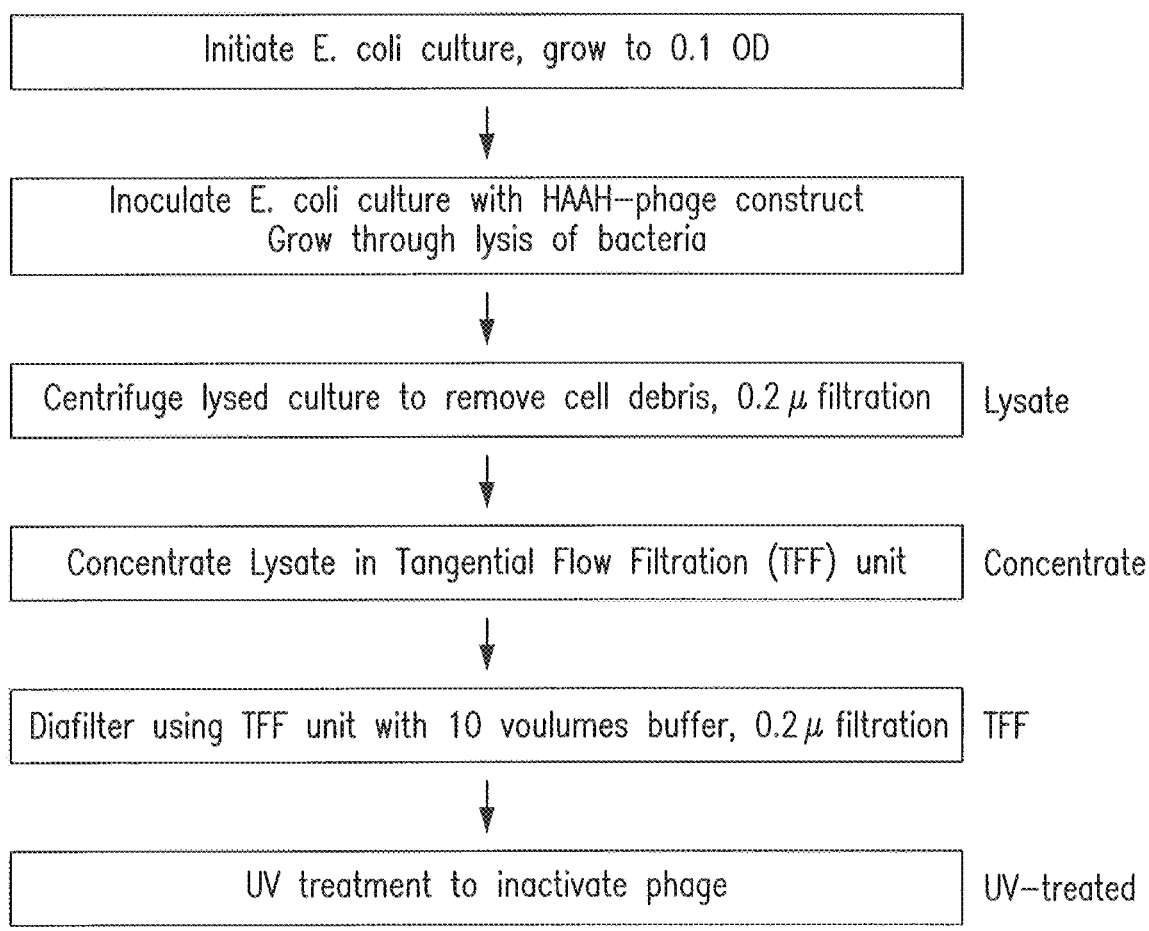
FIG. 7 diagrams one method of growing and purifying constructs in accordance with the present invention.
Figure 8:
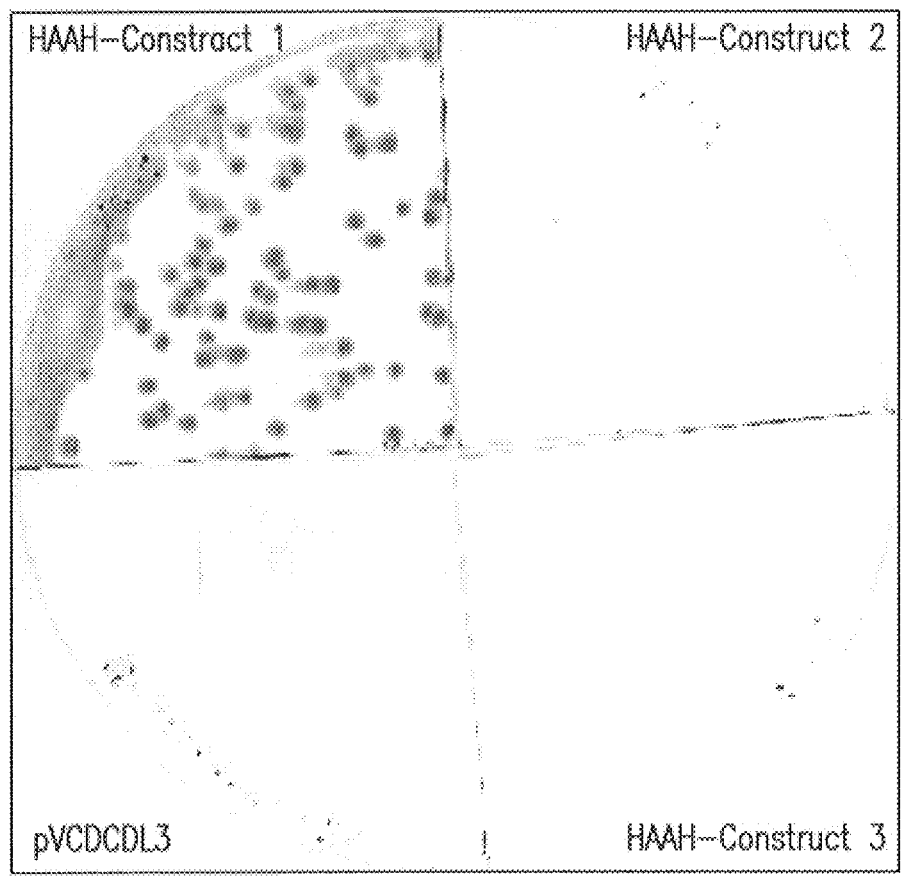
FIG. 8 is an example of a Western blot HAAH-vaccine screening for a cancer vaccine candidate.
Figure 9:
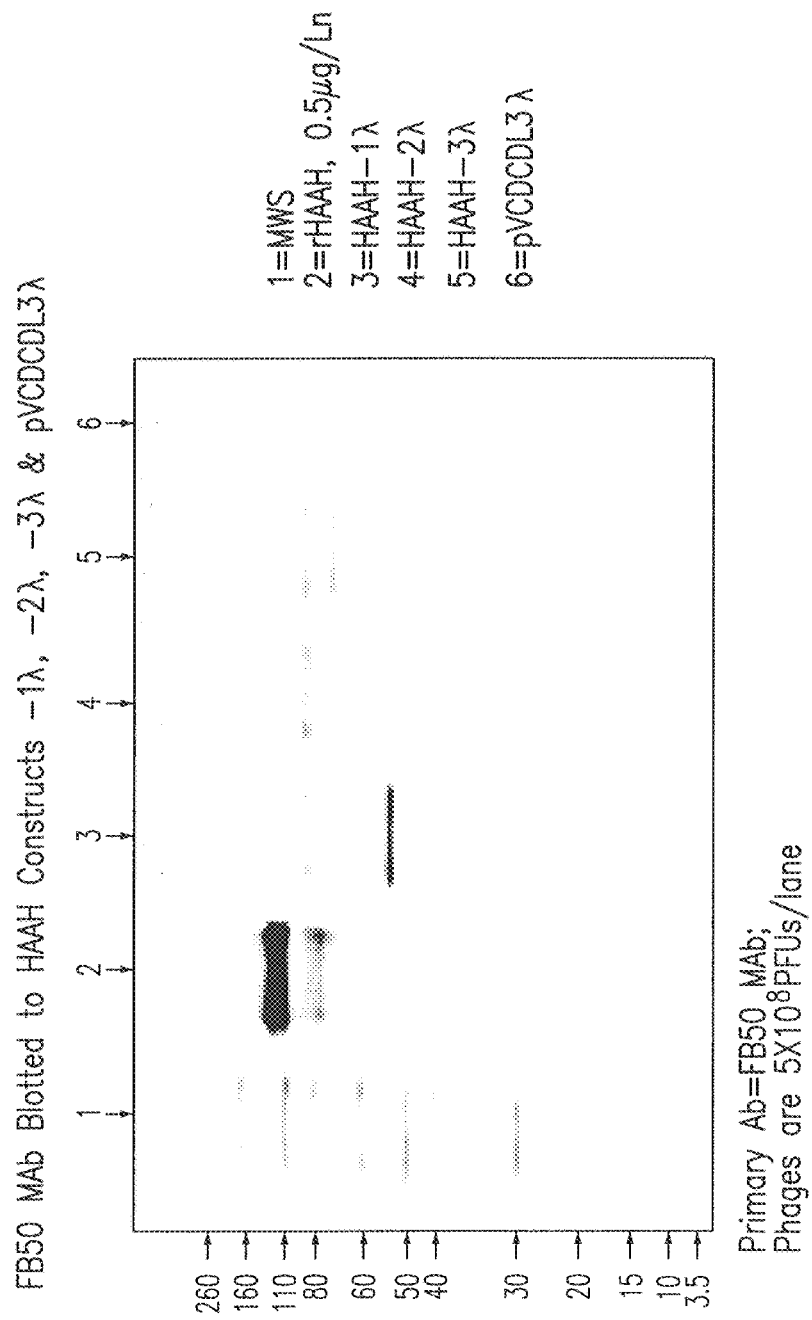
FIG. 9 shows FB50 MAb blotted to HAAH constructs in accordance with the present invention.
Figure 10:
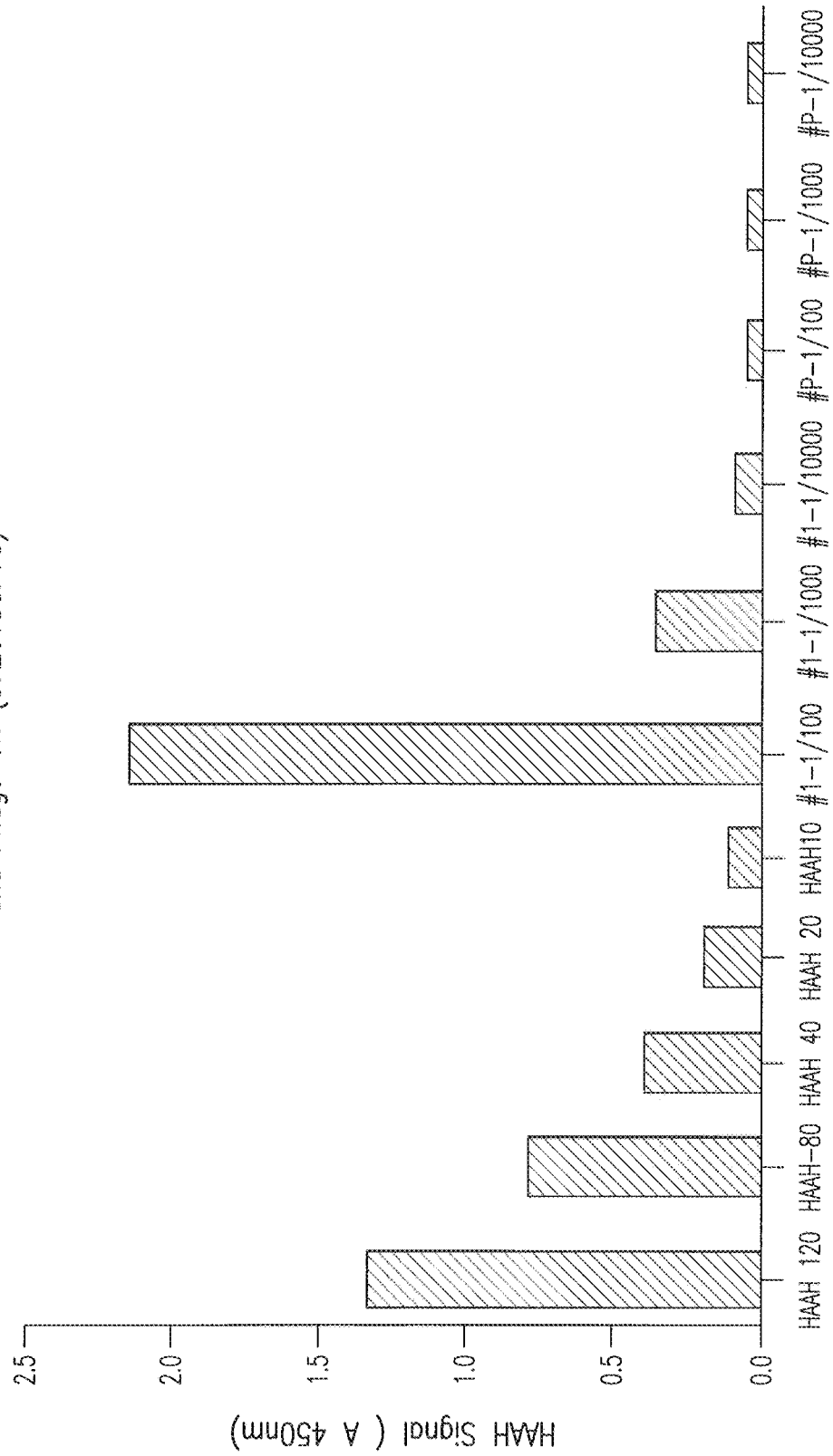
FIG. 10 shows ELISA results.
Figure 11:
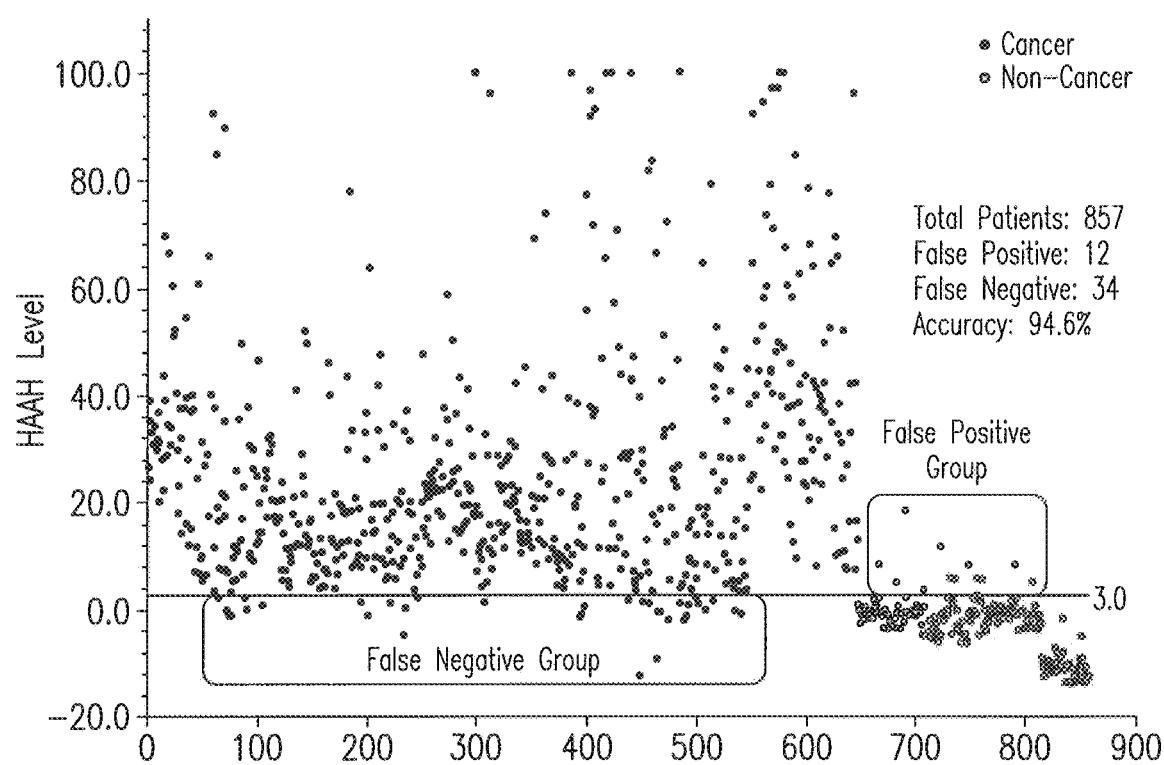
FIG. 11 This scatter chart shows the result of HAAH test as a cancer biomarker on a group of 857 individuals composed of 211 individuals known not to have cancer and 646 patients who are diagnosed with cancer. The cancer group is composed of a mix of individuals with different types of cancer (Breast, Prostate, Lung, Colon) in various stages from one to four. Combining the 12 false positive and 34 false negative results, the test has less than 5.4% error even in such a large group of patients. Horizontal axis is the patient index.
Figure 12:
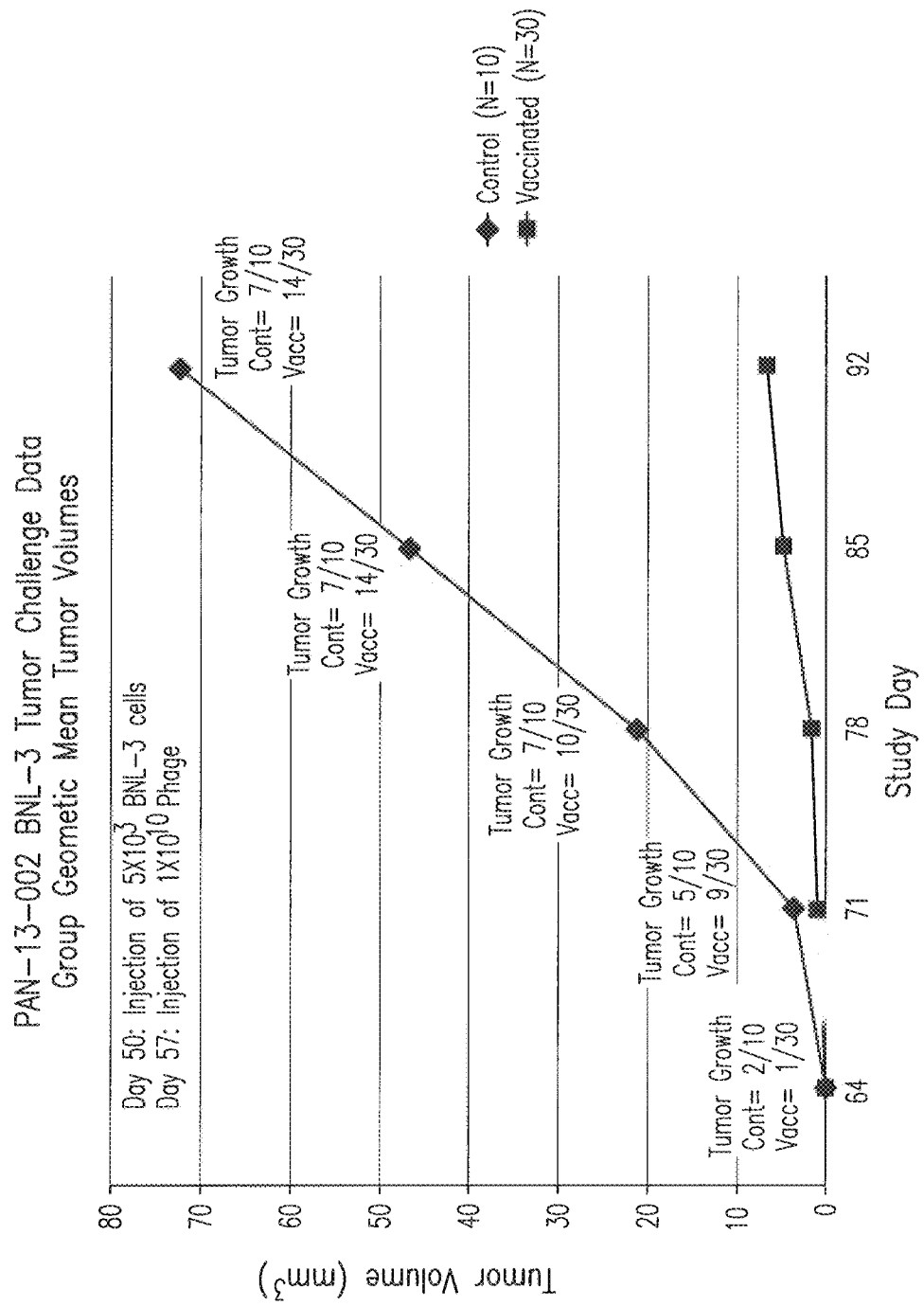
FIG. 12 shows tumor challenge data regarding tumor volume.
Figure 13:
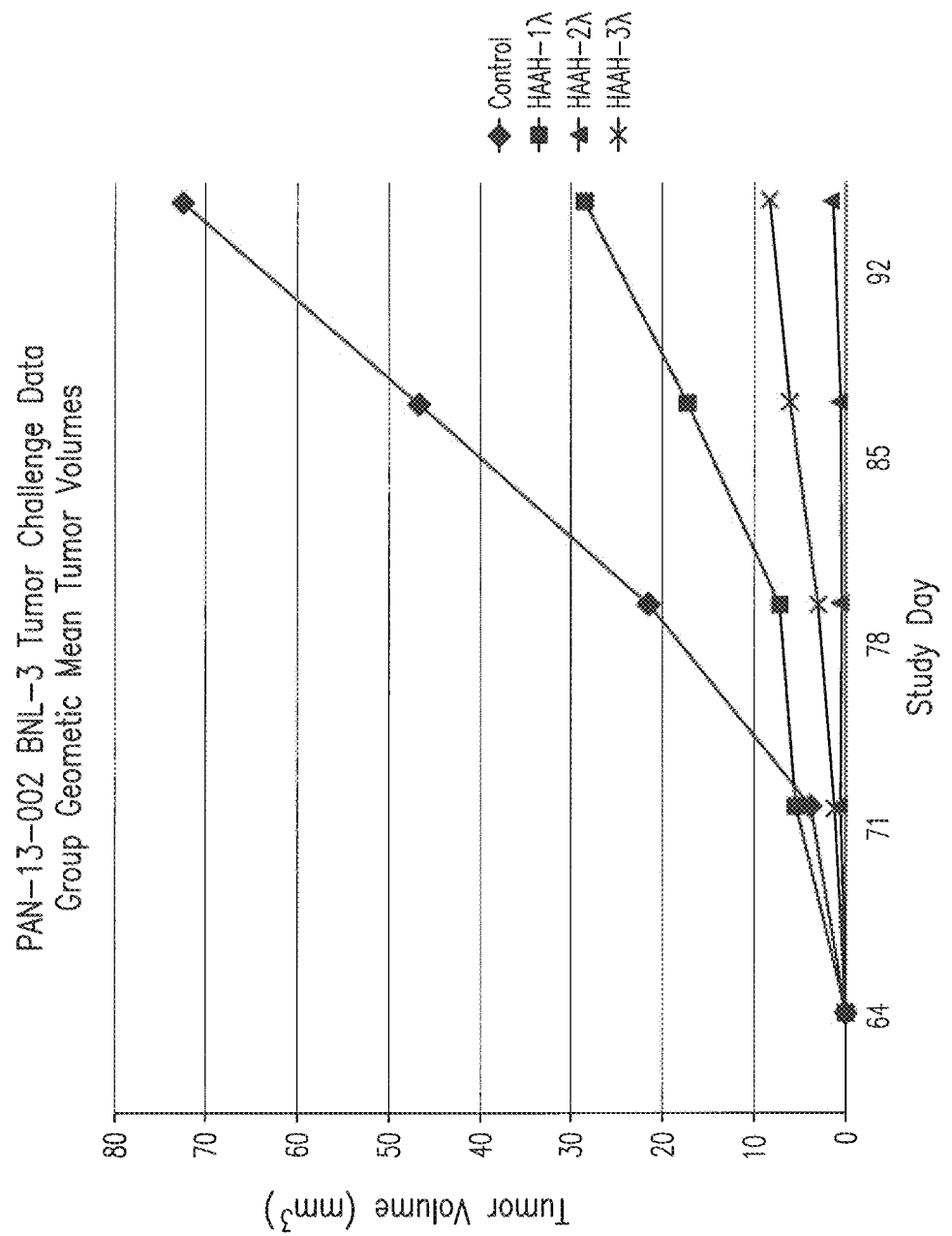
FIG. 13 shows tumor challenge data regarding tumor volume.
Figure 14:
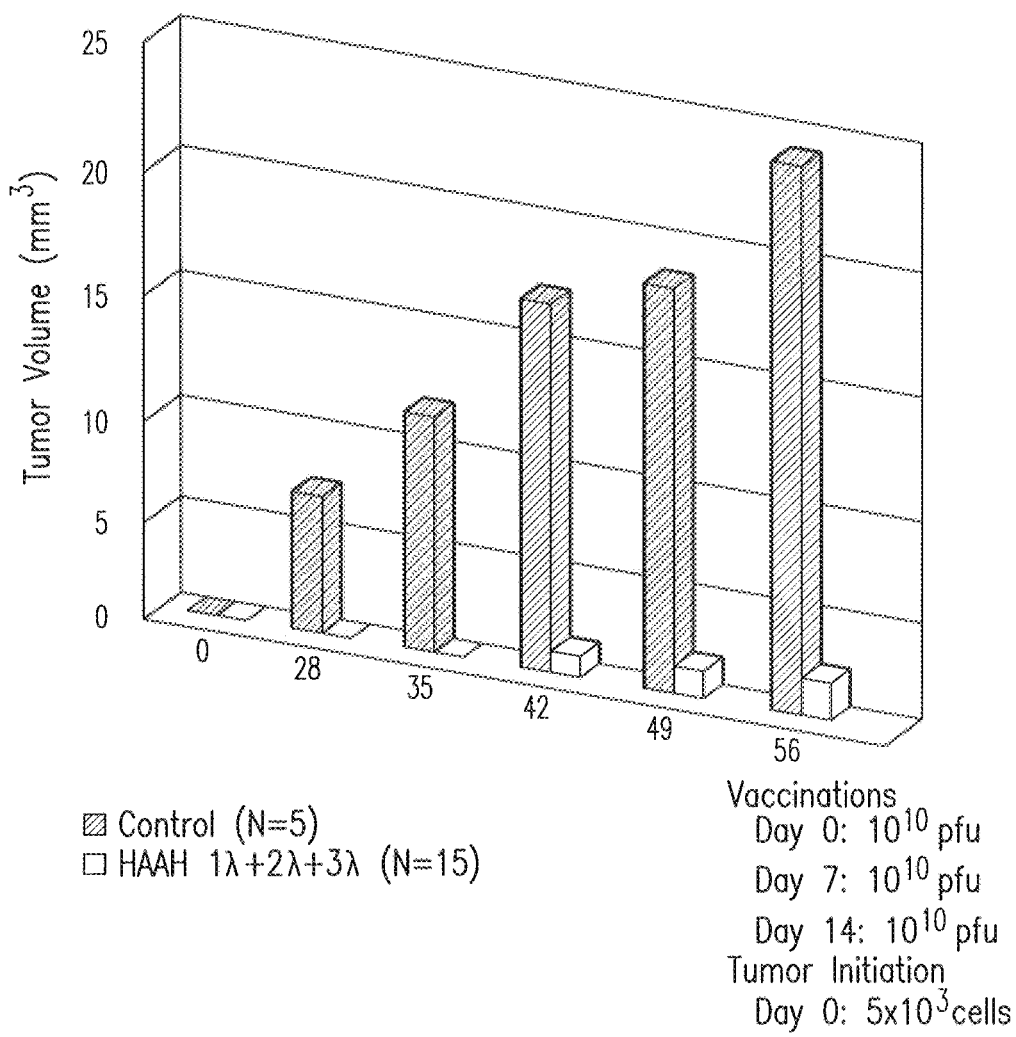
FIG. 14 shows tumor challenge data regarding tumor volume.
Figure 15:
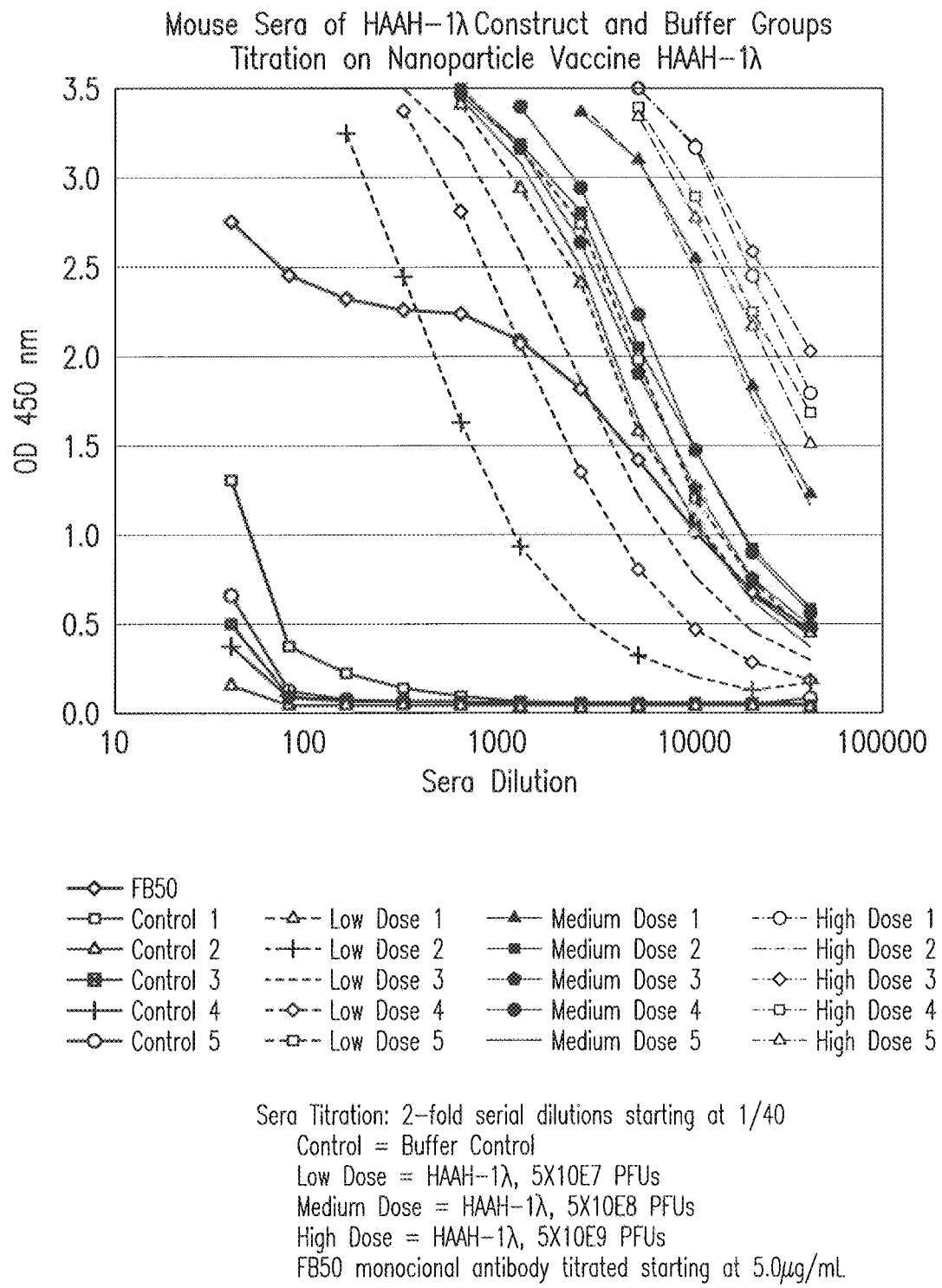
FIG. 15 provides mouse sera data in relation to one embodiment of the present invention.
Figure 16:
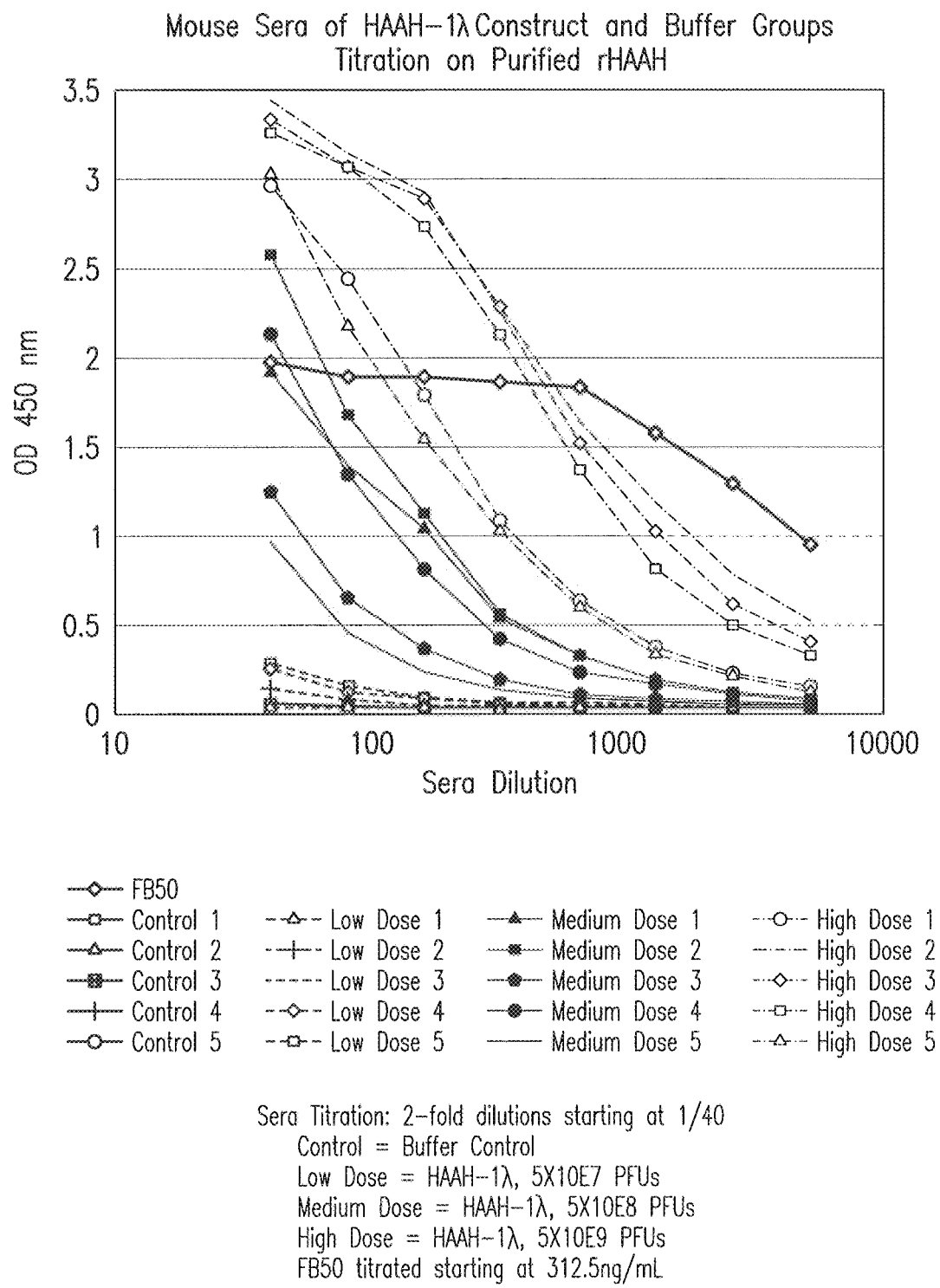
FIG. 16 provides mouse sera data in relation to one embodiment of the present invention.
Figure 17:
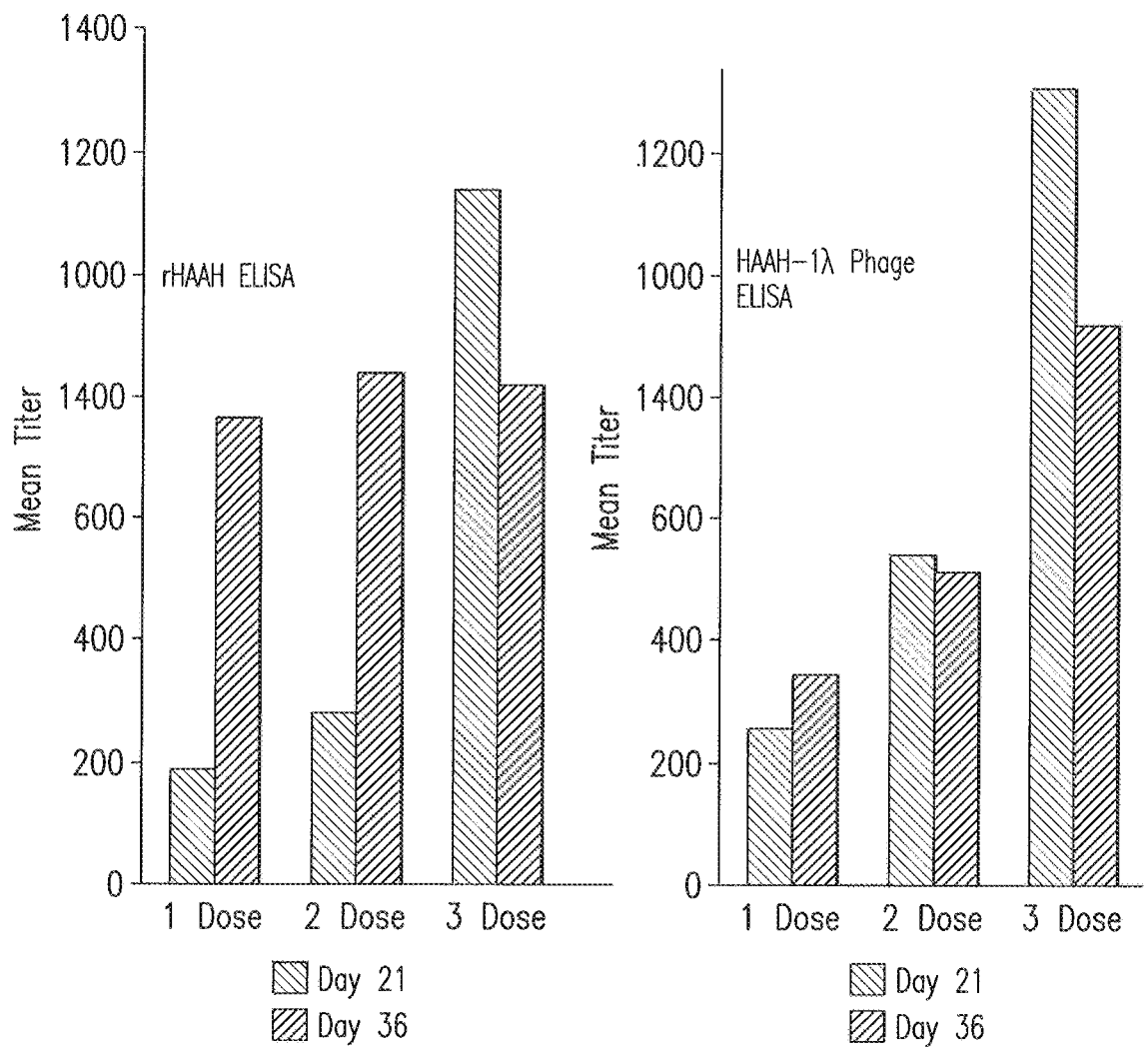
FIG. 17 provides data regarding immunogenicity relative to dose.
Figure 18:
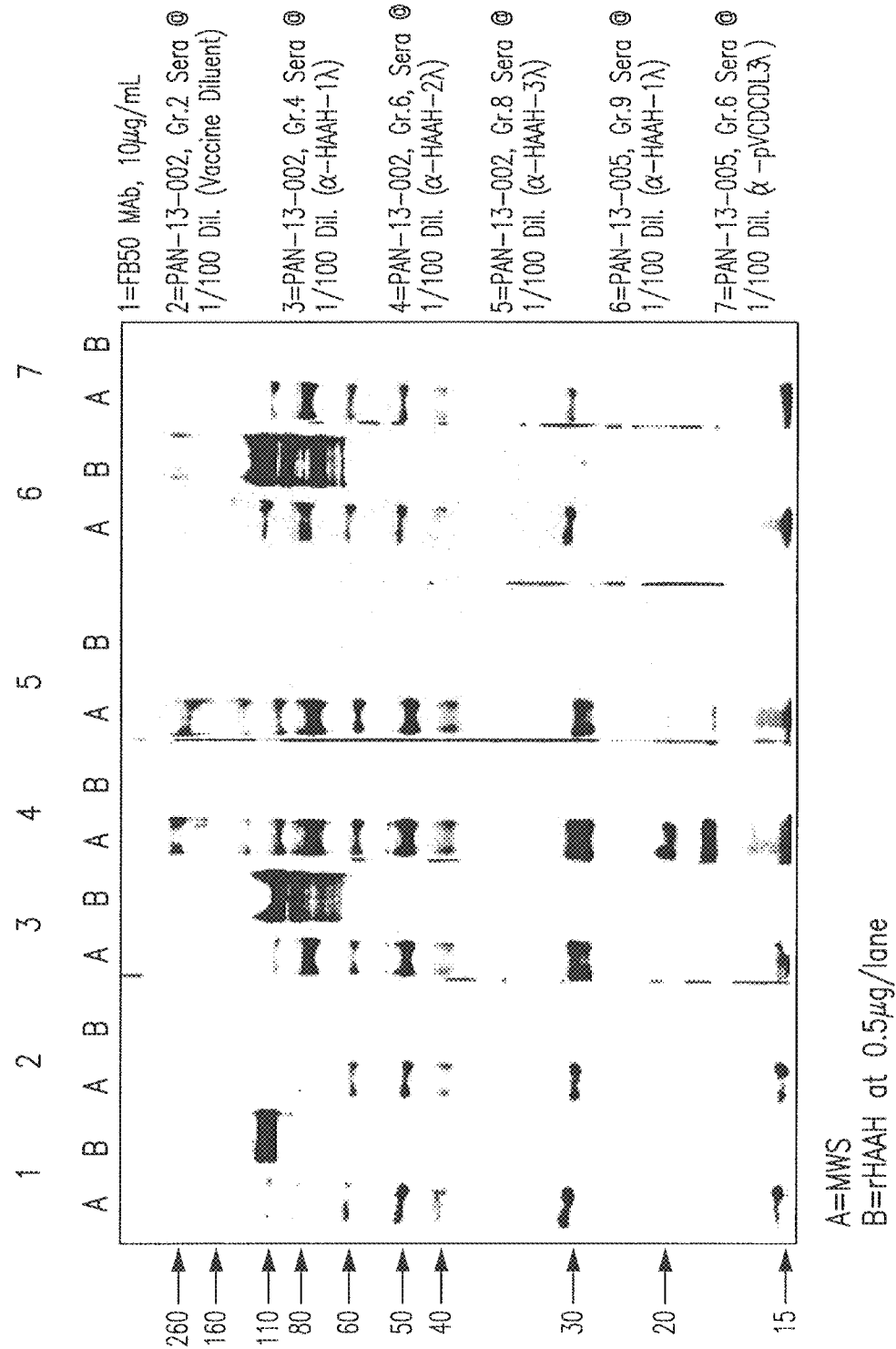
FIG. 18 shows a Western Blot of FB50 and HAAH Sera.

A. Construction of Bacteriophage Lambda for Display of HAAH Peptides:

We designed a bacteriophage lambda system to display HAAH peptides fused at the C terminus of the head protein gpD of phage lambda. Molecular analysis of HAAH reveals a partial amino terminal homology of this protein with other two proteins called Junctin and Humbug. The role of these other two proteins in human physiology is not known completely. To avoid any complication such as activating immune system against these homologous proteins, we specifically eliminated these sequences from our phage display constructs. For proper display of HAAH peptides on lambda head, the rest of the HAAH sequence is segmented in three sections. They are designated as HAAH construct 1, HAAH construct 2 and HAAH construct 3 (see FIG. 7). Using HAAH specific oligo primers these segments are amplified from the HAAH gene which was previously cloned in our laboratory for expression in baculovirus system. The oligo sequence of each PCR primer is modified slightly to produce Nhe I and Bssh II restriction sites in each end of amplified HAAH segments. After restriction digestion, these segments are inserted separately at the NheI-BsshII site of the 3' end of a DNA segment encoding gpD under the control of the lac promoter. The constructs are created in a plasmid vector (donor plasmid pAN-A), which also carries loxPwt and loxP511 sequences. Cre-expressing cells (*E. coli*) are transformed with these recombinant plasmids and subsequently infected with a recipient lambda phage that carries a stuffer DNA segment flanked by loxPwt and loxP511 sites. Recombination occurs in vivo at the lox sites and Ampr cointegrates are formed (FIG. 2), which are spontaneously lyse the *E. coli* and released in culture media. The cointegrates produce recombinant phages that display HAAH peptides fused at the C terminus of gpD. Approximately 200 copies of these peptides are displayed on a single phage head.

B. Selection of Lambda Cointegrates and Production of Recombinant Phages which Display HAAH Peptides:

Lambda cointegrates are selected on Luria Bartani (LB) ampicillin agar (100 ug/ml amp, 15% agar) plates. Briefly, spontaneously lysed *E. coli* culture is used to infect Cre-ve *E. coli* cells and spread on LB ampicillin agar plates. Plates are incubated at 32° C. for 48 hours to obtain Ampr colonies. These Ampr colonies are immune to super infection and carry the phages as plasmid cointegrates. The Ampr colonies containing the lambda cointegrate are grown separately at LB Ampicillin (100 ug/ml) at 37° C. for four hours. Lambda phages are spontaneously induced in these cultures and result in complete lysis. This cell free supernatant is used to infect *E. coli* cells and plated on solid LB agar (15%) plate to obtain phage plaques. The resulting phage plaques are harvested from the plate and single plaques are purified three times on *E. coli* by the standard procedures described by Sambrook et al.

C. Conformation of Lambda Cointegrates Containing HAAH Fragments:

All bacterial colonies, containing lambda cointegrates, which are used for HAAH phage vaccine production are verified by PCR. In this process the presence of each cloned inserts in bacterial colonies are confirmed by PCR amplification of HAAH specific insert DNA by Xba1-5/(TTGGTTAGCAAGTTAATACC) (SEQ ID NO:1) and Xba1-3/(TAGATTTGAATGACTTCCCC) (SEQ ID NO:2) primer set. These two specific primers flank the unique Xba I site of lambda genome and used for PCR the complete insert presence in between Lox recombination sites of lambda DNA.

D. Growth and Purification of Recombinant Phages Displaying HAAH Peptides:

Growth of the plaque purified phages is performed in two steps. The steps are designated as plate lysate method and large scale liquid lysate method. The detail of these procedures are described in Sambrook et al. The lysed culture is chilled at room temperature for further purification by liquid column chromatography technique.

E. Large Scale Purification of Recombinant Lambda-Constructs Using Column Chromatography Technique:

CIM® monolithic columns are an ideal chromatographic support for purifying large biomolecules and nanoparticles, bacterial viruses and plasmid DNA. The pore size of these monolithic columns are adjusted to accommodate even the largest molecules and optimized for very high binding capacities at the highest flow rates. We adopted these monolithic columns for large scale purification of lambda phages displaying HAAR-peptides. In order to obtain infective virus during purification process we investigated chemical conditions that provided the maximal yield of phage and which also preserved high infectivity. This information is necessary to adjust chromatographic methods accordingly to avoid undesired phage deactivation during processing.

HPLC equipment: All experiment is preformed on a gradient AKTA purifier FPLC chromatography system (GE Healthcare) equipped with Unicom 5.1 chromatography software, P-900 FPLC pumps, UPC-900 variable wavelength detector, and FRAC-920 fraction collector. CIM ion exchange chromatography is monitored for UV at 280 nm as well as for conductivity and the gradient profile, associated with marks for point of injection and fraction number. Stationary phase: A strong anion exchange (quaternary amine-QA) methacrylate-based CIM disk monolithic column (BIA Separations, Ljubljana, Slovenia) is used for this purification procedure. Mobile phase: 125 mM $NaH_2PO_4$, pH 7.0 (loading buffer) and 125 mM $NaH_2PO_4$, 1.5 M NaCl, pH 7.0 (elution buffer) of different pH values is used. All buffers is filtered through 0.22 micron pore size filters before use. These strong anion exchange (quaternary amine-QA) methacrylate-based CIM disk monolithic columns is periodically sanitized after processing, by a 2 hour procedure using 1 M NaOH. Processing of phage lysate for QA column analysis: Phage lysates (10 mL) are centrifuged at 12000×g for 10 minutes at 4° C. and the phage containing supernatant is filtered through a 0.22 micron filter prior to loading the phage on the column for chromatography. Collected fractions of 1 mL are analyzed via plaque assay to determine presence of infective phage. Plaque assay data is analyzed to optimize specific conditions for column chromatography purification of display phages. When larger amounts of highly concentrated phage will be required, the linear gradient will be changed into a stepwise gradient where narrower peaks will be achieved and fraction collection will be easier. Based on data from the linear gradient, we will introduce conditions for the stepwise gradient for large scale purification of display phages.

For immunoblot assay each phage constructs are separately plated on LB agar plate to obtain 100 to 150 plaques in each plate. The plates are incubated at 37° C. for 18 hours, until the plaques are about one mm in size. Next, a 137 mm colony/plaque screen membrane (NEN® Research products, Boston, Mass.) is soaked in distilled water and blotted dry on a filter paper. This membrane is carefully placed on the top agar and incubation was continued at 37° C. for another 15 minutes. The membrane is peeled from the agar, and washed three times with Tris saline to remove the debris and bacteria. The plates are then stored at 4° C. and the washed NEN® membranes are blocked with 2% casein solution for 1 hour. After blocking, the membranes are incubated in a casein solution containing 1.25 ug/ml of diluted FB 50 monoclonal antibody. This FB50 HAAH specific monoclonal antibody was previously generated in our laboratory for diagnostic application of prostate cancer. After incubation at room temperature for two hours the membranes are washed twice in Tris saline with 0.05% TRITON™-X 100 (polyethylene glycol p-(1,1,3,3-tetramethylbutyl)-phenyl ether), and once in Tris saline for 15 minutes each. The monoclonal treated membranes are incubated with 2.0 .mu.g/ml of alkaline phosphatase labeled rabbit antimouse IgG (Kirkegaard and Perry) for one hour at room temperature. The membranes are consecutively washed three times in the same way described earlier in this procedure, followed by a final wash with 0.9% NaCL. Finally the membranes are treated with Fast Red and naphthol substrate solution for about 10 minutes and the reaction was stopped by washing the membrane in distilled water. The pink immunoreactive spots corresponds the recombinants expressing HAAH specific peptides on lambda head. For Western blots, purified lambda phage particles were electrophoresed under reducing conditions on 0.1% (w/v) SDS/10% polyacrylamide gel followed by electroblotting onto PVDF membrane (Immobilon, Millipore, Bedford, Mass.). Fusion proteins are detected either 2.5 ug/ml diluted rabbit polyclonal sera raised against recombinant expressed lambda GpD or HAAH specific E6 mouse monoclonal antibody (final concentration 1.25 ug/ml). The rabbit antisera treated membranes are incubated with 2.0 μg/ml of alkaline phosphatase labeled goat anti-rabbit IgG and mouse monoclonal treated membranes are incubated with 2.0 μg/ml of alkaline phosphatase labeled rabbit antimouse IgG for one hour at room temperature. The membranes are consecutively washed three times in the same way described earlier in plaque lift assay. Finally the membranes are treated with Fast Red and naphthol substrate solution for about 10 minutes and the reaction is stopped by washing the membrane in distilled water. immunoreactive lines correspond to the gpD specific recombinant proteins.

Animal Experiments to Evaluate Antigenic Nature of HAAH Phage Vaccine:

A. Study of Antigenicity of HAAH-Phage Vaccine on Female BALB/c Mice.

The purpose of this experiment is to determine the efficacy of HAAH-phage vaccine to elicit antibody response in BALB/c female mice. Previously three separate HAAH-lambda phage constructs were prepared where fragmented HAAH antigens are displayed on surface of lambda phage head as fusion of lambda capsid protein gpD. Such three constructs were designated as HAAH construct I, HAAH construct 2, and HAAH construct 3. Four separate groups of mice (Group A, Group B, Group C, 5 mice in each group and Group D, 40 mice) will be injected subcutaneously (s/c) with various HAAH phage constructs as described in chart below (Chart 1). Briefly, group A mice will receive $5 \times 10^8$ pfu of HAAH construct 1 phage particles suspended in 500 μl of sterile PBS. Similarly group B and group C mice will receive same quantity of HAAH construct 2 and HAAH construct 3 phage particles respectively. Group D mice will receive equi-molar mixture of all 3 phage constructs. A fifth group of mice (group E, 40 mice) will receive recombinant HAAH antigen (50 μg/mice) suspended in sterile PBS. As a control (group F, 40 mice) will be injected with wild type phage pAN-A-k. After primary inoculation, mice will receive 1st and 2nd booster (dose will be the same as primary inoculation) of corresponding antigens at 2 weeks interval. All animals will be bled prior primary inoculation. Serum samples will be collected before every booster to monitor progression of immune response against HAAH antigens. After 21 days animal will be euthanized for final bleeding through cardiac puncture. Finally animals will be sacrificed by spinal dislocations. Sera from group D, group E and group F animals will be saved at −70° C. freezer for second animal experiment. During experiment, all animals will be monitored for their health conditions. The immune response against various HAAH-phage vaccines will be monitored by western immunoblot and ELISA.

|      | Groups |      |      |      |      |      |         |
|------|--------|------|------|------|------|------|---------|
| Days | A | B | C | D | E | F | Scoring |
| 0 | HAAH construct 1 $5 \times 10^8$ pfu | HAAH construct 2 $5 \times 10^8$ pfu | HAAH construct 3 $5 \times 10^8$ pfu | Mixture of 3 HAAH constructs $5 \times 10^8$ pfu | Recombinant HAAH 50 μg | pAN-A-A $5 \times 10^8$ pfu | * |
| 7 | HAAH construct 1 $5 \times 10^8$ pfu | HAAH construct 2 $5 \times 10^8$ pfu | HAAH construct 3 $5 \times 10^8$ pfu | Mixture of 3 HAAH constructs $5 \times 10^8$ pfu | Recombinant HAAH 50 μg | pAN-A-A $5 \times 10^8$ pfu |  |
| 14 | HAAH construct 1 $5 \times 10^8$ pfu | HAAH construct 2 $5 \times 10^8$ pfu | HAAH construct 3 $5 \times 10^8$ pfu | Mixture of 3 HAAH constructs $5 \times 10^8$ pfu | Recombinant HAAH 50 μg | pAN-A-A $5 \times 10^8$ pfu |  |
| 21 | Final Bleed | Final Bleed | Final Bleed | Final Bleed | Final Bleed | Final Bleed | * For 21 days |

Scoring:
0—normal,
1—lethargy and ruffled fur,
2—lethargy, ruffled fur and hunchback,
3—lethargy, ruffled fur, hunchback, and partially closed eyes,
4—moribund,
5—dead.

B. Evaluation of Humoral Immunity Response Against HAAH Phage Constructs:

Previously in xenograft models of human primary liver cancer, the initial target disease, treatment with anti-HAAH antibodies reduced cancer tumor size in all animals, and in 75% of cases after four weeks of treatment tumors were kept to a non-detectable size. In a model of tumor metastasis using human colon cancer cells spreading to the liver, treatment with anti-HAAH antibodies greatly reduced the number and size of metastases. These results are highly significant and clearly indicate the utility of anti-HAAH in the treatment of human cancer. It is noteworthy that in both these instances animals were treated with antibody alone, not in conjunction with any other treatment. In this experiment, 4 groups of nude mice (Group A, Group B and Group C, and group D, 5 mice in each group) will be injected subcutaneously with a primary human liver cancer in their left flank. After 72 hours Group A, Group B and Group C nude mice will be treated by intraperitoneal (i/p) route with 300 ul of sera previously collected from Group D, Group E and Group F mice of 1st animal experiment respectively. As a control Group D nude mice will be receive 300 ul of PBS. The treatment will continue every 48 hours for an additional 4 weeks. After that, the animal will be monitored for another 2 weeks without any intervention. The progression of the tumor will be monitored in treated and control groups every 48 hours to evaluate the result. Finally animals will be sacrificed by spinal dislocations and their organ will be examined by a pathologist for metastasis.

Example 1

Presently, we have designed, developed and produced and lambda-phage based therapeutic anticancer vaccine (nanoparticle) targeting human (Asparaginyl)-β-hydroxylase (HAAH). To overcome the self-antigen tolerance of the HAAH molecule, we have designed a vaccine entity that contains an immunostimulant and present the HAAH in a manner that is unfamiliar to the body. We have expressed three portions of the HAAH protein, sequences from the N-terminus, middle portion, and C-terminus as fusion proteins (with the gpD bacteriophage antigen) on the surface of bacteriophage lambda, generating 200-300 copies per phage. These vaccine entities were characterized and are readily and routinely produced at a level of 1012 plaque forming units (pfu) per liter of E. coli culture. The bacteriophage vaccines have been successfully isolated and purified using tangential flow filtration, a highly scalable process, as well as by PEG precipitation followed by exhaustive dialysis. Both of these processes have reduced bacterial endotoxins to levels within FDA guidelines for formulated human doses. The ease and yield of the manufacturing process allow production of approximately 100 human doses (based on anticipated dose requirements for immunogenicity in human subjects) per liter of culture. The bacteriophage can be rendered non-infectious by ultraviolet radiation; hence it is referred to as nano-particle based vaccine.

TABLE 1

Growth and Purification Data for HAAH Lambda Phage Constructs

| HAAH Construct | HAAH-1λ | HAAH-2λ | HAAH-3λ |
|---|---|---|---|
| Amount Phage in Culture (pfu/L) | $3.5 \times 10^{12}$ | $2.7 \times 10^{12}$ | $5.7 \times 10^{12}$ |
| Purified Phage (pfu/L) and Yield | $2.1 \times 10^{12}$ (58%) | $1.9 \times 10^{12}$ (71%) | $4.0 \times 10^{12}$ (70%) |
| UV-treated Phage (pfu/L) | 0 | — | 0 |
| Nanoparticles/L (infectious + non-infectious phage) | $4.6 \times 10^{13}$ | $9.1 \times 10^{13}$ | $8.6 \times 10^{12}$ |
| Endotoxin (EU/$10^8$ phage) | 156 | 140 | 4 |

Example 2

All three entities display highly significant, dose dependent immunogenicity as assessed by antibody ELISAs. To evaluation the therapeutic effect of the nanoparticle vaccine, we initiated tumor formation in BALB/c mice using a mouse hepatocellular carcinoma line BNLT3. This cell line, a highly tumorigenic subclone of the ATCC cell line, BNL 1ME A.7R.1, was developed by Wands at the Liver Research Center, Rhode Island Hospital by 3 serial subcutaneous passages of the parental cell line. On Day 0 of the tumor challenge study, 4 groups of 5 mice each were administered 5 E03 BNLT3 cells subcutaneously. On the same day, the animal received the first of three weekly subcutaneous doses (at 0, 7, and 14 days) of nanoparticle vaccine as monovalent vaccines of each of the three bacteriophage constructs (10E10 pfu/dose) or a buffer control. The mice were then observed for tumor growth and tumor volume was determined. After 4 weeks (Study Day 28), 3 of 5 mice in the control group had measurable tumor growth, while in the HAAH N terminus, middle portion, and C-terminus construct vaccine groups, 0/5, 2/5, and 0/5 animals, respectively, had measurable tumor growth. The mean tumor volumes of the 5 animals in each of the two groups with tumor growth were 85.8 mm$^3$ for the control group and 24.9 mm$^3$ (29% of the control tumor volume) for the HAAH middle HAAH middle portion group. Overall, the vaccinated groups had 2/15 animals and mean tumor growth of 8.3 mm$^3$ (>10% of the control group tumor size).

Example 3

Immunocompetent mice were used to test immunogenicity of three phage-based vaccine candidates, encompassing the N-terminal, mid, and C-terminal portions of the HAAH extracellular domain. All three entities display highly significant, dose-dependent immunogenicity. Animals were injected with 5×107-5×109 pfus on days 0, 7, and 14. Animals were bled on day 21 and immunogenicity was screened using recombinant HAAH in an ELISA format. Cell-based ELISAs using liver (FOCUS) and lung (H460) cancer cell lines as well as FACS analysis on these lines were performed. The immunized mice sera had clear anti-HAAH (or anti-cancer cell) activity in all tests. Immunogenicity was dose and construct dependent. This work demonstrates that a nano-particle, phage-based vaccine can break immune tolerance to the native HAAH protein and elicit a specific antibody response; indicating that such vaccines may have significant therapeutic value.

While the invention has been described with reference to certain exemplary embodiments thereof, those skilled in the art may make various modifications to the described embodiments of the invention without departing from the scope of the invention. The terms and descriptions used herein are set forth by way of illustration only and not meant as limitations. In particular, although the present invention has been described by way of examples, a variety of compositions and processes would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A nucleic acid construct comprising at least one nucleotide sequence encoding an amino acid sequence native to Aspartyl-[Asparaginyl]-β-hydroxylase and a nucleotide sequence encoding bacteriophage lambda head decoration protein D (gpD), wherein the amino acid sequence native to Aspartyl-[Asparaginyl]-β-hydroxylase is the amino acid sequence of SEQ ID NO: 7.

2. A nucleic acid construct comprising at least one nucleotide sequence encoding an amino acid sequence native to Aspartyl-[Asparaginyl]-β-hydroxylase and a nucleotide sequence encoding gpD, wherein the amino acid sequence native to Aspartyl-[Asparaginyl]-β-hydroxylase is the amino acid sequence of SEQ ID NO: 8.

3. A nucleic acid construct comprising at least one nucleotide sequence encoding an amino acid sequence native to Aspartyl-[Asparaginyl]-β-hydroxylase and a nucleotide sequence encoding gpD, wherein the amino acid sequence native to Aspartyl-[Asparaginyl]-β-hydroxylase is the amino acid sequence of SEQ ID NO: 9.

4. A recombinant Lambda phage comprising the nucleic acid construct of claim 1.

5. A recombinant Lambda phage comprising the nucleic acid construct of claim 2.

6. A recombinant Lambda phage comprising the nucleic acid construct of claim 3.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttggttagca agttaatacc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tagatttgaa tgacttcccc                                                    20

<210> SEQ ID NO 3
<211> LENGTH: 756
<212> TYPE: PRT
<213> ORGANISM: Homo sapiens

<400> SEQUENCE: 3

Met Ala Gln Arg Lys Asn Ala Lys Ser Ser Gly Asn Ser Ser Ser Ser
1               5                   10                  15

Gly Ser Gly Ser Gly Ser Thr Ser Ala Gly Ser Ser Ser Pro Gly Ala
            20                  25                  30

Arg Arg Glu Thr Lys His Gly Gly His Lys Asn Gly Arg Lys Gly Gly
        35                  40                  45

Leu Ser Gly Thr Ser Phe Phe Thr Trp Phe Met Val Ile Ala Leu Leu
    50                  55                  60

Gly Val Trp Thr Ser Val Ala Val Val Trp Phe Asp Leu Val Asp Tyr
65                  70                  75                  80

Glu Glu Val Leu Gly Lys Leu Gly Ile Tyr Asp Ala Asp Gly Asp Gly
                85                  90                  95

Asp Phe Asp Val Asp Asp Ala Lys Val Leu Leu Gly Leu Lys Glu Arg
            100                 105                 110

Ser Thr Ser Glu Pro Ala Val Pro Pro Glu Glu Ala Glu Pro His Thr
        115                 120                 125

Glu Pro Glu Glu Gln Val Pro Val Glu Ala Glu Pro Gln Asn Ile Glu
    130                 135                 140

Asp Glu Ala Lys Glu Gln Ile Gln Ser Leu Leu His Glu Met Val His
145                 150                 155                 160

Ala Glu His Val Glu Gly Glu Asp Leu Gln Gln Glu Asp Gly Pro Thr
                165                 170                 175

Gly Glu Pro Gln Gln Glu Asp Asp Glu Phe Leu Met Ala Thr Asp Val
            180                 185                 190

Asp Asp Arg Phe Glu Thr Leu Glu Pro Glu Val Ser His Glu Glu Thr
        195                 200                 205

Glu His Ser Tyr His Val Glu Glu Thr Val Ser Gln Asp Cys Asn Gln
    210                 215                 220

Asp Met Glu Glu Met Met Ser Glu Gln Glu Asn Pro Asp Ser Ser Glu

```
            225                 230                 235                 240

Pro Val Val Glu Asp Glu Arg Leu His His Asp Thr Asp Asp Val Thr
                        245                 250                 255

Tyr Gln Val Tyr Glu Glu Gln Ala Val Tyr Glu Pro Leu Glu Asn Glu
                        260                 265                 270

Gly Ile Glu Ile Thr Glu Val Thr Ala Pro Pro Glu Asp Asn Pro Val
                        275                 280                 285

Glu Asp Ser Gln Val Ile Val Glu Glu Val Ser Ile Phe Pro Val Glu
                        290                 295                 300

Glu Gln Gln Glu Val Pro Pro Glu Thr Asn Arg Lys Thr Asp Asp Pro
    305                 310                 315                 320

Glu Gln Lys Ala Lys Val Lys Lys Lys Pro Lys Leu Leu Asn Lys
                        325                 330                 335

Phe Asp Lys Thr Ile Lys Ala Glu Leu Asp Ala Ala Glu Lys Leu Arg
                        340                 345                 350

Lys Arg Gly Lys Ile Glu Glu Ala Val Asn Ala Phe Lys Glu Leu Val
                        355                 360                 365

Arg Lys Tyr Pro Gln Ser Pro Arg Ala Arg Tyr Gly Lys Ala Gln Cys
                        370                 375                 380

Glu Asp Asp Leu Ala Glu Lys Arg Arg Ser Asn Glu Val Leu Arg Gly
    385                 390                 395                 400

Ala Ile Glu Thr Tyr Gln Glu Val Ala Ser Leu Pro Asp Val Pro Ala
                        405                 410                 415

Asp Leu Leu Lys Leu Ser Leu Lys Arg Arg Ser Asp Arg Gln Gln Phe
                        420                 425                 430

Leu Gly His Met Arg Gly Ser Leu Leu Thr Leu Gln Arg Leu Val Gln
                        435                 440                 445

Leu Phe Pro Asn Asp Thr Ser Leu Lys Asn Asp Leu Gly Val Gly Tyr
                        450                 455                 460

Leu Leu Ile Gly Asp Asn Asp Asn Ala Lys Lys Val Tyr Glu Glu Val
    465                 470                 475                 480

Leu Ser Val Thr Pro Asn Asp Gly Phe Ala Lys Val His Tyr Gly Phe
                        485                 490                 495

Ile Leu Lys Ala Gln Asn Lys Ile Ala Glu Ser Ile Pro Tyr Leu Lys
                        500                 505                 510

Glu Gly Ile Glu Ser Gly Asp Pro Gly Thr Asp Asp Gly Arg Phe Tyr
                        515                 520                 525

Phe His Leu Gly Asp Ala Met Gln Arg Val Gly Asn Lys Glu Ala Tyr
                        530                 535                 540

Lys Trp Tyr Glu Leu Gly His Lys Arg Gly His Phe Ala Ser Val Trp
    545                 550                 555                 560

Gln Arg Ser Leu Ile Asn Val Asn Gly Leu Lys Ala Gln Pro Thr Pro
                        565                 570                 575

Lys Glu Thr Gly Tyr Thr Gln Leu Val Lys Ser Leu Glu Arg Asn Trp
                        580                 585                 590

Lys Leu Ile Arg Asp Glu Gly Leu Ala Val Met Asp Lys Ala Lys Gly
                        595                 600                 605

Leu Phe Leu Pro Glu Asp Glu Asn Leu Arg Glu Lys Gly Asp Trp Ser
                        610                 615                 620

Gln Phe Thr Leu Trp Gln Gln Gly Arg Arg Asn Glu Asn Ala Cys Lys
    625                 630                 635                 640

Gly Ala Pro Lys Thr Cys Thr Leu Leu Glu Lys Phe Pro Glu Thr Thr
                        645                 650                 655
```

-continued

```
Gly Cys Arg Arg Gly Gln Ile Lys Tyr Ser Ile Met His Pro Gly Thr
            660                 665                 670

His Val Trp Pro His Thr Gly Pro Thr Asn Cys Arg Leu Arg Met His
        675                 680                 685

Leu Gly Leu Val Ile Pro Lys Glu Gly Cys Lys Ile Arg Cys Ala Asn
    690                 695                 700

Glu Thr Lys Thr Trp Glu Glu Gly Lys Val Leu Ile Phe Asp Asp Ser
705                 710                 715                 720

Phe Glu His Glu Val Trp Gln Asp Ala Ser Ser Phe Arg Leu Ile Phe
                725                 730                 735

Ile Val Asp Val Trp His Pro Glu Leu Thr Pro Gln Gln Arg Arg Ser
            740                 745                 750

Leu Pro Ala Ile
        755

<210> SEQ ID NO 4
<211> LENGTH: 657
<212> TYPE: PRT
<213> ORGANISM: Rattus norvegicus

<400> SEQUENCE: 4

Met Val Ile Ala Leu Leu Gly Val Trp Thr Ser Val Ala Val Val Trp
1               5                   10                  15

Phe Asp Leu Val Asp Tyr Glu Glu Val Leu Gly Lys Leu Gly Val Tyr
                20                  25                  30

Asp Ala Asp Gly Asp Gly Asp Phe Asp Val Asp Ala Lys Val Leu
            35                  40                  45

Leu Gly Leu Lys Glu Arg Ser Thr Ser Glu Arg Thr Phe Pro Pro Glu
    50                  55                  60

Glu Ala Glu Thr Gln Ala Glu Leu Glu Glu Gln Ala Pro Glu Gly Ala
65                  70                  75                  80

Glu Ala Gln Asn Val Glu Asp Glu Val Lys Glu Gln Ile Gln Ser Leu
                85                  90                  95

Leu Gln Glu Ser Val His Thr Asp His Asp Leu Glu Ala Asp Gly Pro
            100                 105                 110

Ala Gly Glu Pro Gln Ser Glu Val Glu Asp Phe Leu Thr Ala Thr Asp
        115                 120                 125

Ser Asp Asp Arg Phe Glu Ala Leu Glu Pro Gly Thr Val His Glu Asp
    130                 135                 140

Thr Glu Asp Ser Tyr His Val Glu Glu Thr Ala Ser Gln Asn His Pro
145                 150                 155                 160

Asn Asp Ala Glu Glu Val Met Ser Glu Gln Glu Ser Ser Glu Glu Val
                165                 170                 175

Arg His Glu Asp Tyr Asp Glu Pro Val Tyr Glu Pro Ser Glu Asn Glu
            180                 185                 190

Arg Ile Glu Ile Ser Asp Asn Ala Ile Asp Ser Asn Ile Ile Ser
        195                 200                 205

Glu Glu Ile Asn Val Ala Ser Val Glu Gln Gln Asp Thr Pro Pro
    210                 215                 220

Val Lys Lys Lys Lys Pro Lys Leu Leu Asn Lys Phe Asp Lys Thr Ile
225                 230                 235                 240

Lys Ala Glu Leu Asp Ala Ala Glu Lys Leu Arg Lys Arg Gly Lys Ile
                245                 250                 255

Glu Glu Ala Val Ser Ala Phe Glu Glu Leu Val Arg Arg Tyr Pro Gln
```

```
                260                 265                 270
Ser Pro Arg Ala Arg Tyr Gly Lys Ala Gln Cys Glu Asp Asp Leu Ala
        275                 280                 285
Glu Lys Gln Arg Ser Asn Glu Val Leu Arg Arg Ala Ile Glu Thr Tyr
        290                 295                 300
Gln Glu Ala Ala Ser Leu Pro Asp Ala Pro Thr Asp Leu Val Lys Leu
305                 310                 315                 320
Ser Leu Lys Arg Arg Ser Glu Arg Gln Gln Phe Leu Gly His Met Arg
                325                 330                 335
Gly Ser Leu Leu Thr Leu Gln Arg Leu Val Gln Leu Phe Pro Ser Asp
                340                 345                 350
Thr Thr Leu Lys Asn Asp Leu Gly Val Gly Tyr Leu Leu Met Gly Asp
                355                 360                 365
Asn Asp Ser Ala Lys Lys Val Tyr Glu Glu Val Leu Asn Val Thr Pro
                370                 375                 380
Asn Asp Gly Phe Ala Lys Val His Tyr Gly Phe Ile Leu Lys Ala Gln
385                 390                 395                 400
Asn Arg Ile Ala Glu Ser Ile Pro Tyr Leu Lys Glu Gly Ile Glu Ser
                405                 410                 415
Gly Asp Pro Gly Thr Asp Asp Gly Arg Phe Tyr Phe His Leu Gly Asp
                420                 425                 430
Ala Met Gln Arg Val Gly Asn Lys Glu Ala Tyr Lys Trp Tyr Glu Leu
                435                 440                 445
Gly His Lys Arg Gly His Phe Ala Ser Val Trp Gln Arg Ser Leu Tyr
                450                 455                 460
Asn Val Asn Gly Leu Lys Ala Gln Pro Trp Trp Thr Pro Arg Glu Thr
465                 470                 475                 480
Gly Tyr Thr Glu Leu Val Lys Ser Leu Glu Arg Asn Trp Lys Leu Ile
                485                 490                 495
Arg Asp Glu Gly Leu Met Val Met Asp Lys Ala Lys Gly Leu Phe Leu
                500                 505                 510
Pro Glu Asp Glu Asn Leu Arg Glu Lys Gly Asp Trp Ser Gln Phe Thr
                515                 520                 525
Leu Trp Gln Gln Gly Arg Lys Asn Glu Asn Ala Cys Lys Gly Ala Pro
                530                 535                 540
Lys Thr Cys Thr Leu Leu Glu Lys Phe Ser Glu Thr Thr Gly Cys Arg
545                 550                 555                 560
Arg Gly Gln Ile Lys Tyr Ser Ile Met His Pro Gly Thr His Val Trp
                565                 570                 575
Pro His Thr Gly Pro Thr Asn Cys Arg Leu Arg Met His Leu Gly Leu
                580                 585                 590
Val Ile Pro Lys Glu Gly Cys Lys Ile Arg Cys Ala Asn Glu Thr Arg
                595                 600                 605
Ser Trp Glu Glu Gly Lys Val Leu Ile Phe Asp Asp Ser Phe Glu His
                610                 615                 620
Glu Val Trp Gln Asp Ala Ser Ser Phe Arg Leu Ile Phe Ile Val Asp
625                 630                 635                 640
Val Trp His Pro Glu Leu Thr Pro Gln Gln Arg Arg Ser Leu Pro Ala
                645                 650                 655
Ile

<210> SEQ ID NO 5
<211> LENGTH: 725
```

<212> TYPE: PRT
<213> ORGANISM: Mus musculus

<400> SEQUENCE: 5

```
Met Ala Pro Arg Lys Asn Ala Lys Gly Gly Gly Asn Ser Ser Ser
 1               5                  10                  15

Ser Gly Ser Gly Ser Gly Ser Gly Ser Pro Ser Thr Gly Ser
            20                  25                  30

Ser Gly Ser Ser Ser Ser Pro Gly Ala Arg Arg Glu Ala Lys His Gly
            35                  40                  45

Gly His Lys Asn Gly Arg Arg Gly Gly Ile Ser Gly Ser Phe Phe
        50                  55                  60

Thr Trp Phe Met Val Ile Ala Leu Leu Gly Val Trp Thr Ser Val Ala
65                  70                  75                  80

Val Val Trp Phe Asp Leu Val Asp Tyr Glu Glu Val Leu Gly Lys Leu
                85                  90                  95

Gly Val Tyr Asp Ala Asp Gly Asp Gly Asp Phe Asp Val Asp Asp Ala
                100                 105                 110

Lys Val Leu Leu Gly Leu Lys Glu Arg Ser Pro Ser Glu Arg Thr Phe
                115                 120                 125

Pro Pro Glu Glu Glu Ala Glu Thr His Ala Glu Leu Glu Glu Gln Ala
130                 135                 140

Pro Glu Gly Ala Asp Ile Gln Asn Val Glu Asp Glu Val Lys Glu Gln
145                 150                 155                 160

Ile Gln Ser Leu Leu Gln Glu Ser Val His Thr Asp His Asp Leu Glu
                165                 170                 175

Ala Asp Gly Leu Ala Gly Glu Pro Gln Pro Glu Val Glu Asp Phe Leu
                180                 185                 190

Thr Val Thr Asp Ser Asp Asp Arg Phe Glu Asp Leu Glu Pro Gly Thr
                195                 200                 205

Val His Glu Glu Ile Glu Asp Thr Tyr His Val Glu Asp Thr Ala Ser
                210                 215                 220

Gln Asn His Pro Asn Asp Met Glu Glu Met Thr Asn Glu Gln Glu Asn
225                 230                 235                 240

Ser Glu Glu Val Arg His Gln Asp Tyr Asp Glu Pro Val Tyr Glu Pro
                245                 250                 255

Ser Glu His Glu Gly Val Ala Ile Ser Asp Asn Thr Ile Asp Asp Ser
                260                 265                 270

Ser Ile Ile Ser Glu Glu Ile Asn Val Ala Ser Val Glu Gln Gln
                275                 280                 285

Asp Thr Pro Pro Val Lys Lys Lys Pro Lys Leu Leu Asn Lys Phe
290                 295                 300

Asp Lys Thr Ile Lys Ala Glu Leu Asp Ala Glu Lys Leu Arg Lys
305                 310                 315                 320

Arg Gly Lys Ile Glu Glu Ala Val Asn Ala Phe Glu Glu Leu Val Arg
                325                 330                 335

Lys Tyr Pro Gln Ser Pro Arg Ala Arg Tyr Gly Lys Ala Gln Cys Glu
                340                 345                 350

Asp Asp Leu Ala Glu Lys Gln Arg Ser Asn Glu Val Leu Arg Arg Ala
                355                 360                 365

Ile Glu Thr Tyr Gln Glu Ala Ala Asp Leu Pro Asp Ala Pro Thr Asp
                370                 375                 380

Leu Val Lys Leu Ser Leu Lys Arg Arg Ser Glu Arg Gln Gln Phe Leu
385                 390                 395                 400
```

Gly His Met Arg Gly Ser Leu Leu Thr Leu Gln Arg Leu Val Gln Leu
             405                 410                 415

Phe Pro Ser Asp Thr Thr Leu Lys Asn Asp Leu Gly Val Gly Tyr Leu
            420                 425                 430

Leu Leu Gly Asp Asn Asp Ser Ala Lys Lys Val Tyr Glu Glu Val Leu
            435                 440                 445

Asn Val Thr Pro Asn Asp Gly Phe Ala Lys Val His Tyr Gly Phe Ile
450                 455                 460

Leu Lys Ala Gln Asn Lys Ile Ser Glu Ser Ile Pro Tyr Leu Lys Glu
465                 470                 475                 480

Gly Ile Glu Ser Gly Asp Pro Gly Thr Asp Asp Gly Arg Phe Tyr Phe
            485                 490                 495

His Leu Gly Asp Ala Met Gln Arg Val Gly Asn Lys Glu Ala Tyr Lys
            500                 505                 510

Trp Tyr Glu Leu Gly His Lys Arg Gly His Phe Ala Ser Val Trp Gln
            515                 520                 525

Arg Ser Leu Tyr Asn Val Asn Gly Leu Lys Ala Gln Pro Trp Trp Thr
            530                 535                 540

Pro Arg Glu Thr Gly Tyr Thr Glu Leu Val Lys Ser Leu Glu Arg Asn
545                 550                 555                 560

Trp Lys Leu Ile Arg Asp Glu Gly Leu Met Val Met Asp Lys Ala Lys
                565                 570                 575

Gly Leu Phe Leu Pro Glu Asp Glu Asn Leu Arg Glu Lys Gly Asp Trp
            580                 585                 590

Ser Gln Phe Thr Leu Trp Gln Gln Gly Arg Lys Asn Glu Asn Ala Cys
            595                 600                 605

Lys Gly Ala Pro Lys Thr Cys Ala Leu Leu Glu Lys Phe Ser Glu Thr
            610                 615                 620

Thr Gly Cys Arg Arg Gly Gln Ile Lys Tyr Ser Ile Met His Pro Gly
625                 630                 635                 640

Thr His Val Trp Pro His Thr Gly Pro Thr Asn Cys Arg Leu Arg Met
                645                 650                 655

His Leu Gly Leu Val Ile Pro Lys Glu Gly Cys Lys Ile Arg Cys Ala
            660                 665                 670

Asn Glu Thr Arg Thr Trp Glu Glu Gly Lys Val Leu Ile Phe Asp Asp
            675                 680                 685

Ser Phe Glu His Glu Val Trp Gln Asp Ala Ser Ser Phe Arg Leu Ile
            690                 695                 700

Phe Ile Val Asp Val Trp His Pro Glu Leu Thr Pro Gln Gln Arg Arg
705                 710                 715                 720

Ser Leu Pro Ala Ile
            725

<210> SEQ ID NO 6
<211> LENGTH: 724
<212> TYPE: PRT
<213> ORGANISM: Gallus gallus

<400> SEQUENCE: 6

Met Ala Ser Arg Lys Gly Ser Lys Gly Thr Gly Gly Ala Pro Gly Pro
1               5                   10                  15

Gly Ser Lys Arg Glu Ser Lys His Gly Gly Asn Arg Asn Gly Lys Lys
            20                  25                  30

Glu Gly Leu Ser Gly Ser Ser Phe Phe Thr Trp Phe Met Val Ile Ala

-continued

```
                35                  40                  45
Leu Leu Gly Val Trp Thr Ser Val Ala Val Trp Phe Glu Leu Val
         50                  55                  60

Asp Tyr Glu Val Leu Ala Lys Ala Lys Asp Phe Arg Tyr Asn Leu
65                  70                  75                  80

Ser Glu Val Leu Gln Gly Lys Leu Gly Ile Tyr Asp Ala Asp Gly
                        85                  90                  95

Gly Asp Phe Asp Val Glu Asp Ala Lys Val Leu Gly Leu Lys Glu
                100                 105                 110

Arg Ser Val Pro Glu Gln Pro Ala Ser Pro Val Ser Glu Glu Thr Ile
                115                 120                 125

Gln Pro Ala Glu Gln Ser Phe Thr Lys Ser Glu His Lys Asn Val Asp
            130                 135                 140

Val Glu Leu Glu Glu Ile Gln Pro Val Leu His Asp Ala Leu His
145                 150                 155                 160

Ser Gln Pro Asp Ala Asp Phe Val Ala Asp Pro Gly Ala Thr Glu
                    165                 170                 175

Pro Glu Thr Tyr Glu Val Pro Gly Asp Ser Glu Leu Thr Leu Glu Asp
                180                 185                 190

Ala Val Glu His Tyr Thr Glu Pro Glu Tyr Glu Lys Glu Thr Glu Thr
            195                 200                 205

Gln Asp Thr Ala Val Glu Asp Leu Pro Glu Glu Val His Glu Ala Thr
210                 215                 220

Glu Pro Val Arg Asp Glu Thr Val Glu Asp Leu Glu Met Glu Lys Lys
225                 230                 235                 240

Leu Pro Val Val Glu Ser Lys His Thr Glu Glu Asp Asn Val Ala Thr
                    245                 250                 255

Gly Pro Glu Glu Ser Glu Val Pro Val Gln Thr Glu Asp Tyr Ser Asn
                260                 265                 270

Asp Asn Leu Val Gly Lys Gly Glu Thr Glu Thr Glu Gln Asp Lys Met
            275                 280                 285

Glu Lys Val Lys Lys Lys Lys Pro Lys Leu Leu Asn Lys Phe Asp
        290                 295                 300

Lys Thr Ile Lys Ala Glu Leu Asp Ala Ala Glu Lys Leu Arg Lys Lys
305                 310                 315                 320

Gly Lys Val Glu Glu Ala Leu Arg Ala Phe Glu Ala Leu Val Asn Gln
                325                 330                 335

Tyr Pro Glu Ser Pro Arg Ala Arg Tyr Gly Lys Ala Gln Ser Glu Asp
                340                 345                 350

Asp Leu Ala Glu Lys Met Arg Ser Asn Glu Met Leu Gln Lys Ala Ile
            355                 360                 365

Asn Thr Tyr Asp Glu Val Val Ser Leu Pro Asn Val Pro Ser Asp Leu
        370                 375                 380

Ile Lys Leu Ser Leu Lys Arg Glu Ala Asp Arg Gln Gln Phe Leu Gly
385                 390                 395                 400

Arg Met Arg Gly Ser Leu Ile Thr Leu Gln Lys Leu Val His Leu Phe
                405                 410                 415

Pro Ser Asp Thr Ser Phe Lys Asn Asp Leu Gly Val Gly Tyr Leu Leu
                420                 425                 430

Ile Gly Asp Asn Ser Asn Ala Lys Gln Val Tyr Glu Glu Val Leu Arg
            435                 440                 445

Met Ala Pro Asp Asp Gly Phe Ala Lys Val His Tyr Gly Phe Ile Leu
        450                 455                 460
```

Lys Ala Glu Asn Lys Ile Ala Glu Ser Ile Pro Tyr Leu Lys Glu Gly
465                 470                 475                 480

Leu Glu Ser Gly Asp Pro Gly Thr Asp Gly Arg Phe Tyr Phe His
            485                 490                 495

Leu Gly Asp Ala Leu Gln Arg Ile Gly Asp Lys Glu Ala Tyr Lys Trp
            500                 505                 510

Tyr Glu Leu Gly Tyr Gln Arg Gly His Phe Ala Ser Val Trp Gln Arg
            515                 520                 525

Ser Leu Tyr Asn Val Lys Gly Leu Lys Ala Gln Pro Trp Trp Thr Ala
530                 535                 540

Lys Glu Thr Gly Tyr Thr Glu Leu Val Lys Ser Leu Glu Lys Asn Trp
545                 550                 555                 560

Lys Leu Ile Arg Asp Glu Gly Leu Asp Val Met Asp Lys Lys Arg Ser
                565                 570                 575

Leu Phe Leu Pro Glu Asp Glu Asn Leu Arg Glu Lys Gly Asp Trp Ser
            580                 585                 590

Gln Phe Thr Leu Trp Gln Gln Gly Arg Lys Asn Glu Asn Ala Cys Lys
            595                 600                 605

Gly Val Pro Lys Thr Cys Ala Leu Leu Glu Arg Phe Pro Glu Ala Thr
610                 615                 620

Gly Cys Arg Arg Gly Gln Ile Lys Tyr Ser Val Met Leu Pro Gly Thr
625                 630                 635                 640

His Val Trp Pro His Thr Gly Pro Thr Asn Cys Arg Leu Arg Met His
                645                 650                 655

Leu Gly Leu Val Ile Pro Lys Glu Gly Cys Arg Ile Arg Cys Ala Gln
            660                 665                 670

Glu Asn Arg Thr Trp Glu Glu Gly Lys Val Leu Ile Phe Asp Asp Ser
            675                 680                 685

Phe Glu His Glu Val Trp Gln Asp Ala Glu Ser Tyr Arg Leu Ile Phe
690                 695                 700

Ile Val Asp Val Trp His Pro Glu Leu Thr Ala Gln Gln Arg Arg Thr
705                 710                 715                 720

Leu Pro Ala Ile

<210> SEQ ID NO 7
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Arg Ala Met Ala Gln Arg Lys Asn Ala Lys Ser Ser Gly Asn Ser
1               5                   10                  15

Ser Ser Ser Gly Ser Gly Ser Gly Ser Thr Ser Ala Gly Ser Ser Ser
            20                  25                  30

Pro Gly Ala Arg Arg Glu Thr Lys His Gly Gly His Lys Asn Gly Arg
            35                  40                  45

Lys Gly Gly Leu Ser Gly Thr Ser Phe Phe Thr Trp Phe Met Val Ile
50                  55                  60

Ala Leu Leu Gly Val Trp Thr Ser Val Ala Val Val Trp Phe Asp Leu
65                  70                  75                  80

Val Asp Tyr Glu Glu Val Leu Gly Lys Leu Gly Ile Tyr Asp Ala Asp
                85                  90                  95

```
Gly Asp Gly Asp Phe Asp Val Asp Asp Ala Lys Val Leu Leu Gly Leu
            100                 105                 110

Lys Glu Arg Ser Thr Ser Glu Pro Ala Val Pro Glu Glu Ala Glu
            115                 120                 125

Pro His Thr Glu Pro Glu Gln Val Pro Val Glu Ala Glu Pro Gln
            130                 135                 140

Asn Ile Glu Asp Glu Ala Lys Glu Gln Ile Gln Ser Leu Leu His Glu
145                 150                 155                 160

Met Val His Ala Glu His Val Glu Gly Glu Asp Leu Gln Gln Glu Asp
                165                 170                 175

Gly Pro Thr Gly Glu Pro Gln Gln Glu Asp Asp Glu Phe Leu Met Ala
                180                 185                 190

Thr Asp Val Asp Asp Arg Phe Glu Thr Leu Glu Pro Glu Val Ser His
            195                 200                 205

Glu Glu Thr Glu His Ser Tyr His Val Glu Glu Thr Val Ser Gln Asp
            210                 215                 220

Cys Asn Gln Asp Met Glu Glu Met Met Ser Glu Gln Glu Asn Pro Asp
225                 230                 235                 240

Ser Ser Glu Pro Val Val Glu Asp Glu Arg Leu His His Asp Thr Asp
                245                 250                 255

Asp Val Thr Tyr Gln Val Tyr Glu Glu Gln Ala Val Tyr Glu Pro Leu
                260                 265                 270

Glu Asn Glu Gly Ile Glu Ile Thr Glu Val Thr Ala Pro Pro Glu Asp
            275                 280                 285

Asn Pro Val Glu Asp Ser Gln Val Ile Val Glu Val Ser Ile Phe
            290                 295                 300

Pro Val Glu Glu Gln Gln Glu Val Pro Pro
305                 310

<210> SEQ ID NO 8
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Asp Ala Ala Glu Lys Leu Arg Lys Arg Gly Lys Ile Glu Glu Ala
1               5                   10                  15

Val Asn Ala Phe Lys Glu Leu Val Arg Lys Tyr Pro Gln Ser Pro Arg
            20                  25                  30

Ala Arg Tyr Gly Lys Ala Gln Cys Glu Asp Asp Leu Ala Glu Lys Arg
        35                  40                  45

Arg Ser Asn Glu Val Leu Arg Gly Ala Ile Glu Thr Tyr Gln Glu Val
    50                  55                  60

Ala Ser Leu Pro Asp Val Pro Ala Asp Leu Leu Lys Leu Ser Leu Lys
65                  70                  75                  80

Arg Arg Ser Asp Arg Gln Gln Phe Leu Gly His Met Arg Gly Ser Leu
                85                  90                  95

Leu Thr Leu Gln Arg Leu Val Gln Leu Phe Pro Asn Asp Thr Ser Leu
            100                 105                 110

Lys Asn Asp Leu Gly Val Gly Tyr Leu Leu Ile Gly Asp Asn Asp Asn
        115                 120                 125

Ala Lys Lys Val Tyr Glu Glu Val Leu Ser Val Thr Pro Asn Asp Gly
```

```
            130                 135                 140
Phe Ala Lys Val His Tyr Gly Phe Ile Leu Lys Ala Gln Asn Lys Ile
145                 150                 155                 160

Ala Glu Ser Ile Pro Tyr Leu Lys Glu Gly Ile Glu Ser Gly Asp Pro
                165                 170                 175

<210> SEQ ID NO 9
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Thr Asp Asp Gly Arg Phe Tyr Phe His Leu Gly Asp Ala Met Gln
1               5                   10                  15

Arg Val Gly Asn Lys Glu Ala Tyr Lys Trp Tyr Glu Leu Gly His Lys
                20                  25                  30

Arg Gly His Phe Ala Ser Val Trp Gln Arg Ser Leu Tyr Asn Val Asn
            35                  40                  45

Gly Leu Lys Ala Gln Pro Trp Trp Thr Pro Lys Glu Thr Gly Tyr Thr
50                  55                  60

Glu Leu Val Lys Ser Leu Glu Arg Asn Trp Lys Leu Ile Arg Asp Glu
65                  70                  75                  80

Gly Leu Ala Val Met Asp Lys Ala Lys Gly Leu Phe Leu Pro Glu Asp
                85                  90                  95

Glu Asn Leu Arg Glu Lys Gly Asp Trp Ser Gln Phe Thr Leu Trp Gln
            100                 105                 110

Gln Gly Arg Arg Asn Glu Asn Ala Cys Lys Gly Ala Pro Lys Thr Cys
        115                 120                 125

Thr Leu Leu Glu Lys Phe Pro Glu Thr Thr Gly Cys Arg Arg Gly Gln
130                 135                 140

Ile Lys Tyr Ser Ile Met His Pro Gly Thr His Val Trp Pro His Thr
145                 150                 155                 160

Gly Pro Thr Asn Cys Arg Leu Arg Met His Leu Gly Leu Val Ile Pro
                165                 170                 175

Lys Glu Gly Cys Lys Ile Arg Cys Ala Asn Glu Thr Arg Thr Trp Glu
            180                 185                 190

Glu Gly Lys Val Leu Ile Phe Asp Asp Ser Phe Glu His Glu Val Trp
        195                 200                 205

Gln Asp Ala Ser Ser Phe Arg Leu Ile Phe Ile Val Asp Val Trp His
    210                 215                 220

Pro Glu Leu Thr Pro Gln Gln Arg Arg Ser Leu Pro Ala Ile
225                 230                 235

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Glu Phe Met Gln Ala Trp Glu Thr
1               5
```